United States Patent
Sarkar et al.

(10) Patent No.: US 10,844,012 B2
(45) Date of Patent: Nov. 24, 2020

(54) ANTIBACTERIAL COMPOUNDS AND METHODS OF USE THEREOF

(71) Applicant: Wayne State University, Detroit, MI (US)

(72) Inventors: Fazlul H. Sarkar, Plymouth, MI (US); Subhash Padhye, Pune (IN); Bernhard Max Biersack, Prebitz (DE); Hossein Salimnia, Rochester Hills, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 16/885,145

(22) Filed: May 27, 2020

(65) Prior Publication Data
US 2020/0283384 A1 Sep. 10, 2020

Related U.S. Application Data

(63) Continuation of application No. 16/085,947, filed as application No. PCT/US2017/023234 on Mar. 20, 2017, now Pat. No. 10,703,716.

(60) Provisional application No. 62/310,481, filed on Mar. 18, 2016.

(51) Int. Cl.

| | |
|---|---|
| *A61P 31/04* | (2006.01) |
| *A61K 31/404* | (2006.01) |
| *C07D 209/10* | (2006.01) |
| *A61K 31/7036* | (2006.01) |
| *A61K 31/4178* | (2006.01) |
| *A61K 31/546* | (2006.01) |
| *A61K 31/7052* | (2006.01) |
| *A61K 31/498* | (2006.01) |
| *A61K 31/5377* | (2006.01) |
| *A61K 31/427* | (2006.01) |
| *A61K 31/4353* | (2006.01) |
| *A61K 38/12* | (2006.01) |
| *A61K 31/407* | (2006.01) |

(52) U.S. Cl.
CPC .......... *C07D 209/10* (2013.01); *A61K 31/404* (2013.01); *A61K 31/407* (2013.01); *A61K 31/4178* (2013.01); *A61K 31/427* (2013.01); *A61K 31/4353* (2013.01); *A61K 31/498* (2013.01); *A61K 31/5377* (2013.01); *A61K 31/546* (2013.01); *A61K 31/7036* (2013.01); *A61K 31/7052* (2013.01); *A61K 38/12* (2013.01); *A61P 31/04* (2018.01); *Y02A 50/30* (2018.01)

(58) Field of Classification Search
CPC .... C07D 209/10; A61K 31/404; A61K 31/43; A61K 2300/00; A61P 31/04
See application file for complete search history.

(56) References Cited

U.S. PATENT DOCUMENTS

| | | | |
|---|---|---|---|
| 8,148,547 | B2 | 4/2012 | Safe |
| 2010/0087504 | A1 | 4/2010 | Tjalkens |
| 2016/0037773 | A1 | 2/2016 | Qian et al. |

OTHER PUBLICATIONS

Bharate, et al., "Discovery of 3,3'-diindolylmethanes as potent antileishmanial agents," European Journal of Medicinal Chemistry, vol. 63, 2013, pp. 435-443.
Khalafi-Nezhad, et al., "L-Proline-modified magnetic nanoparticles (LPMNP): a novel magnetically separable organocatalyst," Royal Society of Chemistry, vol. 4, 2014, pp. 22497-22500.
Letchumanan, et al., "An insight of traditional plasmid curing in Vibrio species," Frontiers in Microbiology, vol. 6, No. 735, 2015, pp. 1-8.
Office Action for U.S. Appl. No. 16/085,947, dated Jun. 28, 2019, Sarkar, "Antibacterial Compounds and Methods of Use Thereof," 9 pages.
Invitation to Pay Additional Fees for Application No. PCT/US2017/023234, dated May 22, 2017, 2 pages.
Search Report & Written Opinion for Application No. PCT/US2017/023234, dated Aug. 7, 2017, 12 pages.
PubChem CID: 2923760 (CMEMBL380528; STK521342; 4-(di-1H-indol-3-ylmethyl)benzene-1,2-diol); Modify Date: Jul. 1, 2017; Create Date: Jul. 29, 2005; https://pubchem.ncbi.nlm.nih.gov/compound/2923760, originally accessed Jul. 5, 2017, 16 pages.
Sarva, et al., "Synthesis, antibacterial and anti-inflammatory activity of bis(indolyl)methanes," Chinese Chemical Letters, vol. 27, No. 1, 2016, pp. 16-20.

*Primary Examiner* — Alicia L Otton
(74) *Attorney, Agent, or Firm* — Tanya Harding; C Rachal Winger

(57) ABSTRACT

Disclosed herein are antibacterial compounds, pharmaceutical compositions including the antibacterial compounds, and methods of treating bacterial infections using the compounds and compositions.

9 Claims, 3 Drawing Sheets

MHA          MHA- Antibiotic

Lane 1: DNA Ladder (3μl)
Lane 2: KSA (Untreated/Parent Strain)
Lane 3: KSA 34 C19
Lane 4: KSA 34 C15
Lane 5: KSA 34 C3
Lane 6: KSA 18 C21
Lane 7: KSA 18 C15
Lane 8: KSA 18 C4
Lane 9: KSA (Untreated/Parent Strain)
Lane 10: KSA (Untreated/Parent Strain)
Lane 11: DNA Ladder (6μl)

ANTIBACTERIAL COMPOUNDS AND METHODS OF USE THEREOF

CROSS-REFERENCE TO RELATED APPLICATION

This is a continuation of co-pending U.S. application Ser. No. 16/085,947, filed Sep. 17, 2018, which is the U.S. National Phase of PCT/US2017/023234, filed Mar. 20, 2017, which claims priority to 62/310,481, filed on Mar. 18, 2016. Each of of these earlier filed applications is incorporated herein by reference in its entirety as if fully set forth herein.

FIELD OF THE DISCLOSURE

The present disclosure provides antibacterial compounds and methods of use thereof. The compositions and methods are particularly useful to treat antibiotic-resistant strains of bacteria.

BACKGROUND OF THE DISCLOSURE

Before antibiotics became widely available in the 1940s, a major cause of death was bacterial infectious disease. This has changed with the availability of antibiotics but bacterial organisms have developed resistance mechanisms faster than the development of new antibiotics. The financial and health costs related to antibiotic resistance are enormous and the consequences of reverting to a pre-antibiotic era are dire.

A high percentage of bacteria that cause bloodstream or lung infections in hospitals have developed resistance to at least one antimicrobial drug. The US and global healthcare systems are now regularly encountering multi-drug resistant (MDR) organisms resistant to most or all known antibiotics. According to a 2008 study, at least 25,000 patients in the European Union die from an infection caused by MDR bacteria and estimated additional health-care costs and productivity losses are at least €1.5 billion. In the U.S., 2 million patients develop MDR health-care associated infections each year and 99,000 die as a result. Direct expenses alone cost between $21 and $34 billion and resistant infections in the US require more than 8 million additional days in the hospital compared to non-resistant infections.

Of particular concern are infections caused by MDR *Staphylococcus*, including *Staphylococcus aureus* (*S. aureus*). While staphylococci can be in 20-30% of healthy adults and in the majority of instances, do not cause disease, damage to the skin or other injury may allow the bacteria to overcome the natural protective mechanisms of the body, leading to infection. Common staphylococcal infections include skin infections, pneumonia, food poisoning, toxic shock syndrome, and blood stream infection (bacteremia).

Methicillin-resistant *S. aureus* (MRSA) infections began to appear in the US in the 1960s, with vancomycin-resistant strains first reported in 2002. Today, the World Health Organization reports that 95% of *S. aureus* infections worldwide are resistant to penicillin and 90% are MRSA.

There are more than 180 antibiotics on the market in the US. A comprehensive study of antibiotic development found that in 2008, only 15 antibiotics of 167 under development had a new mechanism of action with the potential to meet the challenge of MDR. Accordingly, an urgent need exists for the development of new antibiotics that are effective against organisms that are resistant to currently-available antibiotics.

SUMMARY OF THE DISCLOSURE

Disclosed herein are antibacterial compounds useful in the treatment of bacterial infections, including infections caused by multiple-drug resistant (MDR) bacteria. Methods of treating bacterial infections with the compounds and pharmaceutical compositions including the compounds are also disclosed.

DETAILED DESCRIPTION

A high percentage of bacteria that cause bloodstream or lung infections in hospitals have developed resistance to at least one antimicrobial drug. The financial and health costs related to antibiotic resistance are enormous and the consequences of reverting to a pre-antibiotic era are dire.

Figure 1A:
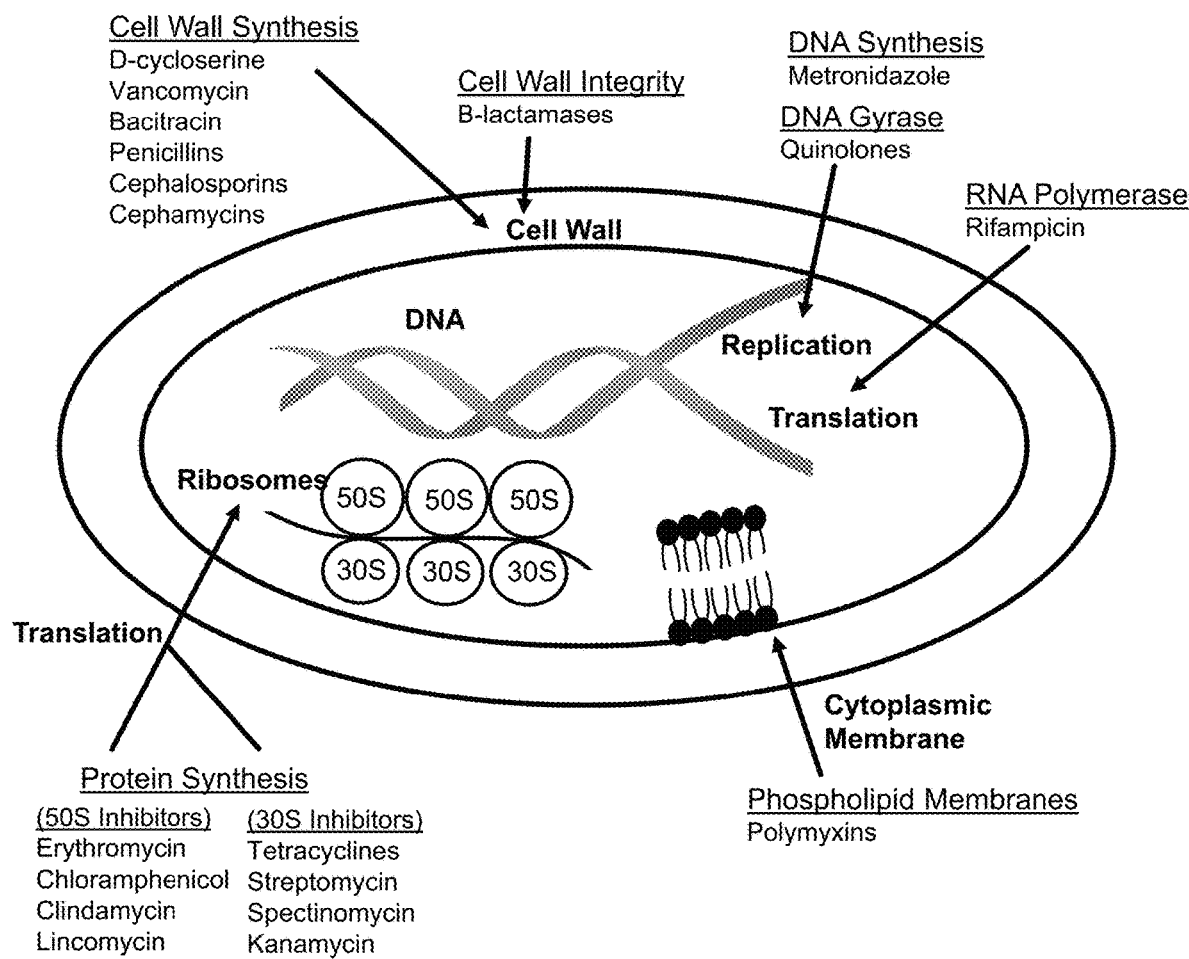
FIG. 1A depicts anti-bacterial mechanisms of action of exemplary antibiotics.
Figure 1B:
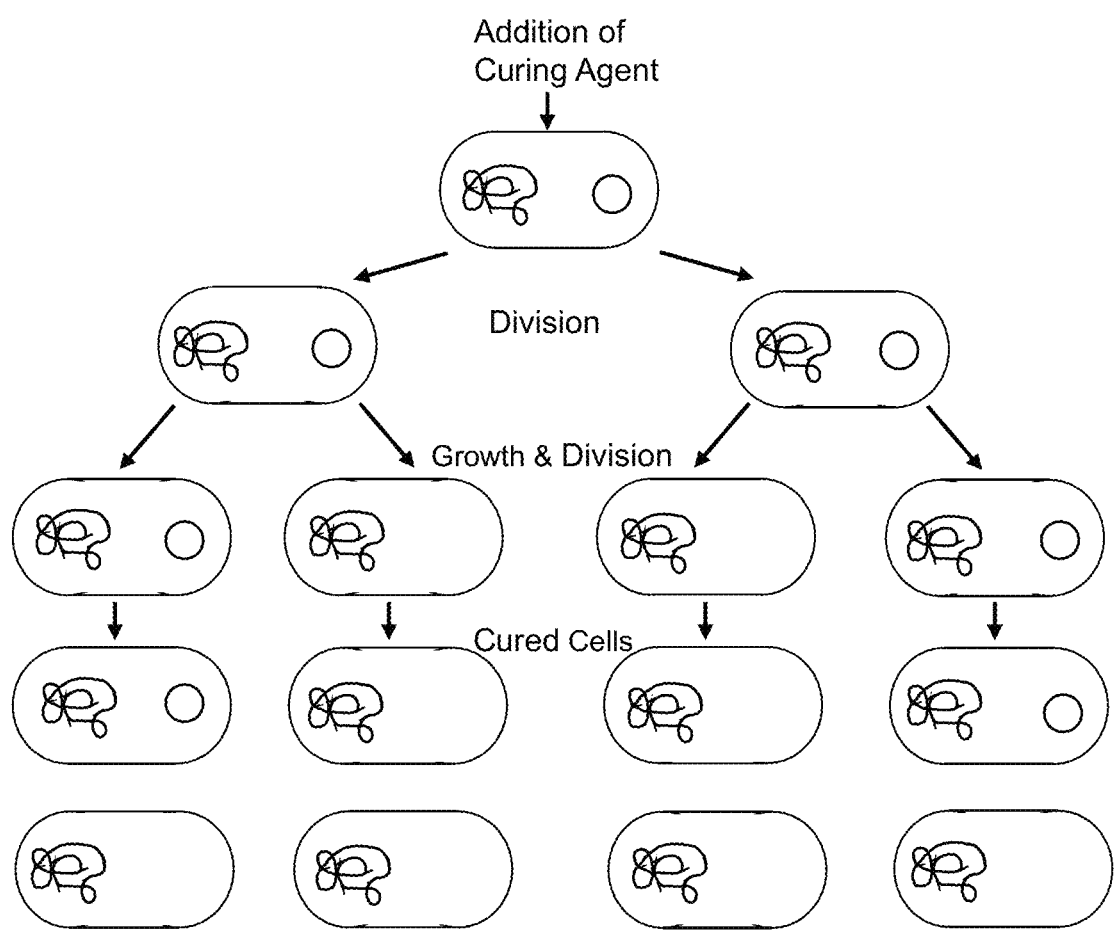
FIG. 1B depicts the mechanism of plasmid curing by elimination of the plasmid carrying the antibiotic resistance gene from antibiotic resistant bacteria.
Figure 2:
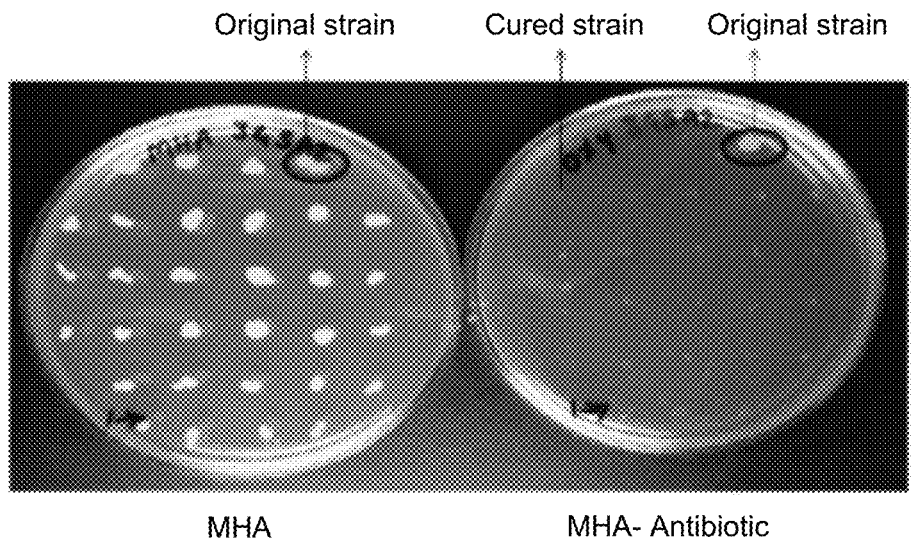
FIG. 2 depicts the phenotypic detection of a plasmid-cured strain of *S. aureus* after exposure to the compound(s) disclosed herein.

FIG. 1A shows some mechanisms of action of exemplary antibiotics. Bacteria share their antibiotic resistance genes with other bacteria, however, by transmittal of plasmid DNA containing resistance genes through various means (pilli formation, etc.). Plasmid curing is a method of removing or destroying these plasmids in bacteria (FIG. 1B). Plasmid curing allows for reversing the antibiotic resistance of bacteria by removal of the resistance genes on the plasmids. Once the plasmids are removed or otherwise destroyed, available antibiotics can be used against the bacteria at physiologic, bioavailable, and non-toxic concentrations. Conventional agents to effect plasmid curing include mutagenic agents, carcinogenic agents, detergents, and physical destruction of the plasmid.

As plasmids are used to convey antibiotic resistance in both gram-positive and gram-negative bacteria, the process of plasmid curing is applicable to both classes of bacteria. Disclosed herein are compositions and methods for treating bacterial infections including compounds capable of targeting plasmids carrying antibiotic resistance genes in bacteria. Accordingly, also disclosed herein are antibacterial compounds useful in the treatment of bacterial infections, including infections caused by multiple-drug resistant (MDR) bacteria. Methods of treating bacterial infections with the compounds and pharmaceutical compositions including the compounds are also disclosed.

Particular embodiments include a compound represented by the following Formula 1:

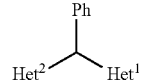

Formula 1 wherein Ph is optionally substituted phenyl; and Het is optionally substituted indolyl; and Het² is optionally substituted indolyl.

Particular embodiments include a compound represented by the following Formula 2:

Formula 2

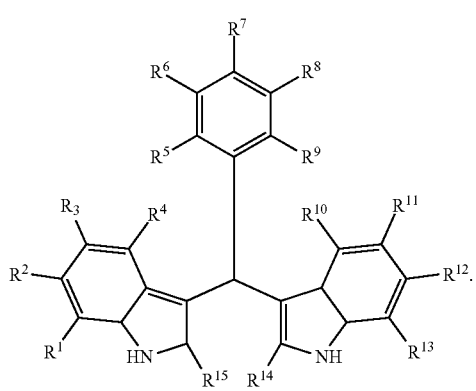

Unless otherwise indicated, when a compound or chemical structural feature such as aryl is referred to as being "optionally substituted," it includes a feature that has no substituents (i.e. unsubstituted), or a feature that is "substituted," meaning that the feature has one or more substituents. The term "substituent" has the broadest meaning known to one of ordinary skill in the art, and includes a moiety that replaces one or more hydrogen atoms in a parent compound or structural feature. The term "replaces" is merely used herein for convenience, and does not require that the compound be formed by replacing one atom with another. In particular embodiments, a substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In particular embodiments, a substituent includes: 0-30, 0-20, 0-10, or 0-5 carbon atoms; and 0-30, 0-20, 0-10, or 0-5 heteroatoms, wherein each heteroatom may independently be: N, O, S, Si, F, Cl, Br, or I; provided that the substituent includes one C, N, O, S, Si, F, Cl, Br, or I atom. A substituent should be sufficiently stable for a compound to be useful for the uses recited herein.

Examples of substituents include, but are not limited to, hydrocarbyl, such as linear branched or cyclic alkyl, alkenyl, or alkynyl; heteroalkyl, including any alkyl wherein one or more heteroatoms replaces one or more carbon atoms, and some accompanying hydrogen atoms (e.g. N replaces CH, O replaces $CH_2$, C replaces $CH_3$, etc.), such as alkoxy, alkylthio, haloalkyl, haloalkoxy, amino, etc.; heteroalkenyl, including any alkenyl wherein one or more heteroatoms replaces one or more carbon atoms, and some accompanying hydrogen atoms, such as acyl, acyloxy, thiocarbonyl, alkylcarboxylate, O-carbamyl, N-carbamyl, O-thiocarbamyl, N-thiocarbamyl, C-amido, N-amido, sulfinyl, isocyanato, isothiocyanato, etc; heteroalkynyl, including any alkynyl wherein one or more heteroatoms replaces one or more carbon atoms, and some accompanying hydrogen atoms, such as cyano, thiocyanato, cyanato; aryl; heteroaryl; hydroxy; aryloxy; thiol; halo; S-sulfonamido; N-sulfonamido; nitro, silyl; sulfonyl; trihalomethanesulfonyl; trihalomethanesulfonamido; etc.

For convenience, the term "molecular weight" refers to the sum of the atomic masses of all the atoms in a molecule. The term is also used with respect to a moiety or part of a molecule to indicate the sum of the atomic masses of the atoms in the moiety or part of a molecule, even though it may not be a complete molecule.

The structures associated with some of the chemical names referred to herein are depicted below. These structures may be unsubstituted, as shown below, or a substituent may independently be in any position normally occupied by a hydrogen atom when the structure is unsubstituted. Unless a point of attachment is indicated by

attachment may occur at any position normally occupied by a hydrogen atom.

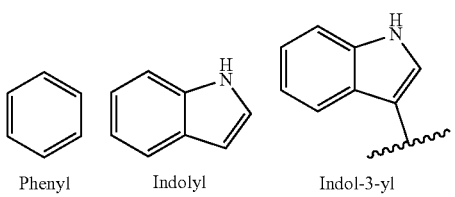

Phenyl      Indolyl      Indol-3-yl

As used herein, the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in particular embodiments, may contain from one to thirty-five carbon atoms. In particular embodiments, alkyl may include $C_{1-10}$ linear alkyl, such as methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3-10}$ branched alkyl, such as $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. heptyl isomers), etc.; $C_{3-10}$ cycloalkyl, such as $C_3H_5$ (e.g. cyclopropyl), $C_4H_7$ (e.g. cyclobutyl isomers such as cyclobutyl, methylcyclopropyl, etc.), $C_5H_9$ (e.g. cyclopentyl isomers such as cyclopentyl, methylcyclobutyl, dimethylcyclopropyl, etc.) $C_6H_{11}$ (e.g. cyclohexyl isomers), $C_7H_{13}$ (e.g. cycloheptyl isomers), etc.; and the like.

If stereochemistry is not indicated, such as in Formulas 1 and 2, a name or structural depiction includes any stereoisomer or any mixture of stereoisomers.

Particular embodiments include an optionally substituted 3-((2,7a-dihydro-1H-indol-3-yl)(phenyl)methyl)-3a,7a-dihydro-1H-indole. Particular embodiments include an optionally substituted 4-((2-methyl-2,7a-dihydro-1H-indol-3-yl)(2-methyl-3a,7a-dihydro-1H-indol-3-yl)methyl)benzene-1,2-diol. Particular embodiments include an optionally substituted 3-((3,4-difluorophenyl)(2,7a-dihydro-1H-indol-3-yl)methyl)-3a,7a-dihydro-1H-indole. Particular embodiments include an optionally substituted 3-((3,4-difluorophenyl)(2-methyl-2,7a-dihydro-1H-indol-3-yl)methyl)-2-methyl-3a,7a-dihydro-1H-indole.

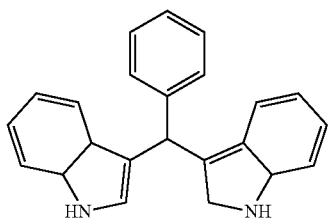

3-((2,7a-dihydro-1H-indol-3-yl)(phenyl)methyl)-3a,7a-dihydro-1H-indole

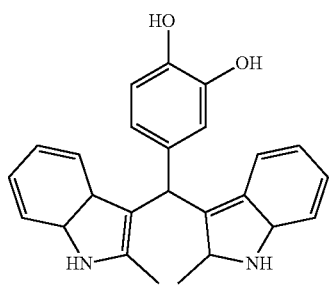

4-((2-methyl-2,7a-dihydro-1H-indol-3-yl)(2-methyl-3a,7a-dihydro-1H-indol-3yl)methyl)benzene-1,2-diol

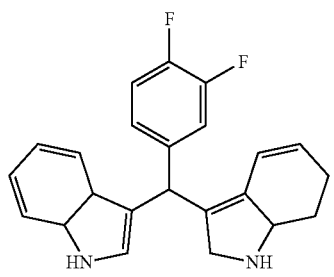

DIM-DF (HN18)

3-((3,4-difluorophenyl)(2,7a-dihydro-1H-indol-3-yl)methyl)-3a,7a-dihydro-1H-indole

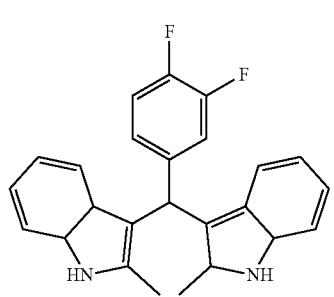

MeDIM-DF (HN34)

3-((3,4-difluorophenyl)(2-methyl-2,7a-dihydro-1H-indol-3-yl)methyl)-2-methyl-3a,7a-dihydro-1H-indole Particular embodiments include (1E,6E)-1,7-bis(4-hydroxy-3-methoxyphenyl)hepta-1,6-diene{4(3,4 difluorobenzylidene)}-3,5-dione.

Formula 3

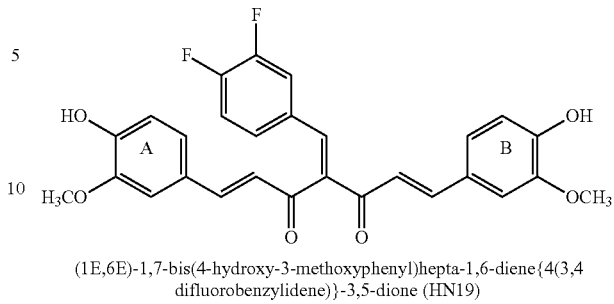

(1E,6E)-1,7-bis(4-hydroxy-3-methoxyphenyl)hepta-1,6-diene{4(3,4 difluorobenzylidene)}-3,5-dione (HN19)

HN19 is a fluorinated curcumin analog. It is characterized by improved bioavailability and anti-cancer activity. The synthesis of HN19 and its therapeutic activity are described in WO 2011/142795 and US 2014/0303109. HN19 is a Knoevanagle condensate that can be reacted with a nitrogen-containing reactant, such as an amine, or a hydrazide, to prepare 3,5-disubstituted Schiff bases. Both HN19 (Knoevanagle condensate and the Schiff base form ligands that will conjugate with a metal ion, such as a Cu(II) ion (WO 2011/142795 and US 2014/0303109).

With respect to any relevant structural representation, such as Formula 1, Ph is an optionally substituted phenyl. If Ph is substituted, it may have 1, 2, 3, 4 or 5 substituents. Any substituent may be included on the phenyl. In particular embodiments, some or all of the substituents on the phenyl may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be $C_{1-20}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-20}$—O-alkyl; $C_{1-20}$ hydroxyalkyl; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In particular embodiments a substituent of Ph is F, OH, or $CH_3$. In particular embodiments, Ph is:

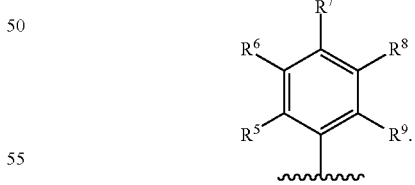

With respect to any relevant structural representation, such as Formula 1, $Het^1$ is optionally substituted indolyl. If Het is substituted, it may have 1, 2, 3, 4, or 5 substituents. Any substituent may be included on $Het^1$. In particular embodiments, some or all of the substituents on the indolyl may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be $C_{1-20}$ alkyl, such as CH$_3$, C$_2$H$_5$, C$_3$H$_7$, cyclic C$_3$H$_5$, C$_4$H$_9$, cyclic C$_4$H$_7$, CH$_{11}$, cyclic C$_5$H$_9$, C$_6$H$_{13}$, cyclic C$_6$H$_{11}$, etc.; C$_{1-20}$—O-alkyl; C$_{1-20}$ hydroxyalkyl; halo, such as F, Cl, Br, I; OH; CN; NO$_2$; C$_{1-6}$ fluoroalkyl, such as CF$_3$, CF$_2$H, C$_2$F, etc.; a C$_{1-10}$ ester such as —O$_2$CCH$_3$, —CO$_2$CH$_3$, —O$_2$CC$_2$H$_5$, —CO$_2$C$_2$H$_5$, —O$_2$C-phenyl, —CO$_2$-phenyl, etc.; a C$_{1-10}$ ketone such as —COCH$_3$, —COC$_2$H$_5$, —COC$_3$H$_7$, —CO-phenyl, etc.; or a C$_{1-10}$ amine such as NH$_2$, NH(CH$_3$), N(CH$_3$)$_2$, N(CH$_3$)C$_2$H$_5$, etc. In particular embodiments a substituent of Het$^1$ is F, OH, or CH$_3$. In particular embodiments, Het$^1$ is:

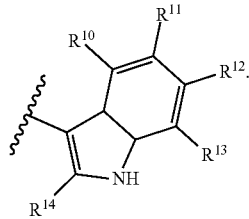

With respect to any relevant structural representation, such as Formula 1, Het$^2$ is optionally substituted indolyl. If Het$^2$ is substituted, it may have 1, 2, 3, 4, or 5 substituents. Any substituent may be included on Het$^2$. In particular embodiments, some or all of the substituents on the indolyl may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be C$_{1-20}$ alkyl, such as CH$_3$, C$_2$H$_5$, C$_3$H$_7$, cyclic C$_3$H$_5$, C$_4$H$_9$, cyclic C$_4$H$_7$, C$_5$H$_{11}$, cyclic C$_5$H$_9$, C$_6$H$_{13}$, cyclic C$_6$H$_{11}$, etc.; C$_{1-20}$—O-alkyl; C$_{1-20}$ hydroxyalkyl; halo, such as F, Cl, Br, I; OH; CN; NO$_2$; C$_{1-6}$ fluoroalkyl, such as CF$_3$, CF$_2$H, C$_2$F$_5$, etc.; a C$_{1-10}$ ester such as —O$_2$CCH$_3$, —CO$_2$CH$_3$, —O$_2$CC$_2$H$_5$, —CO$_2$C$_2$H$_5$, —O$_2$C-phenyl, —CO$_2$-phenyl, etc.; a C$_{1-10}$ ketone such as —COCH$_3$, —COC$_2$H$_5$, —COC$_3$H$_7$, —CO-phenyl, etc.; or a C$_{1-10}$ amine such as NH$_2$, NH(CH$_3$), N(CH$_3$)$_2$, N(CH$_3$)C$_2$H$_5$, etc. In particular embodiments a substituent of Het is F, OH, or CH$_3$. In particular embodiments, Het$^2$ is:

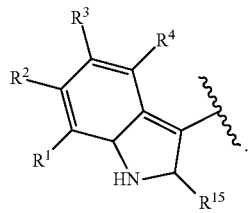

With respect to any relevant structural representation, such as Formula 2; R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, or R$^{15}$, may independently be H or any substituent, such as a substituent having from 0 to 6 carbon atoms and from 0 to 5 heteroatoms, wherein each heteroatom is independently: O, N, S, F, C, Br, or I; and/or having a molecular weight of 15 g/mol to 300 g/mol, or 15 g/mol to 150 g/mol. In particular embodiments, R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, or R$^{15}$, are independently R$^A$, F, C, CN, OR$^A$, CF$_3$, NO$_2$, NR$^A$R$^B$, OR$^A$, CO$_2$R$^A$, OCOR$^A$, NR$^A$COR$^B$, CONR$^A$R$^B$, etc. In particular embodiments, R$^1$, R$^2$, R$^3$, R$^4$, R$^5$, R$^6$, R, R$^8$, R$^9$, R$^{10}$, R$^{11}$, R$^{12}$, R$^{13}$, R$^{14}$, or R$^{15}$, are independently H; F; Cl; CN; CF$_3$; OH; NH$_2$; C$_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or C$_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.

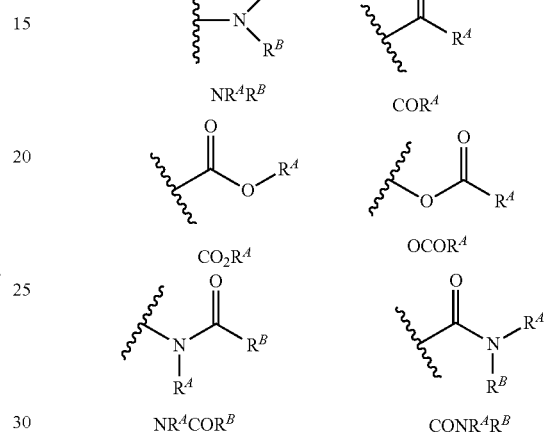

Each R$^A$ may independently be H, or C$_{1-12}$ alkyl, including: linear or branched alkyl having a formula C$_a$H$_{2a+1}$, wherein a is 1, 2, 3, 4, 5, 6, 7, 8, 9, 10, 11, or 12, such as linear or branched alkyl of a formula: CH$_3$, C$_2$H$_5$, C$_3$H$_7$, C$_4$H$_9$, C$_5$H$_{11}$, C$_6$H$_{13}$, C$_7$H$_{15}$, C$_8$H$_{17}$, CH$_{19}$, C$_1$H$_{21}$, etc. Each R$^A$ may also be a cycloalkyl having a formula C$_a$H$_{2a-1}$, wherein a is 3, 4, 5, 6, 7, 8, 9, 10, 11, or 12. In particular embodiments, R$^A$ may be H or C$_{1-6}$ alkyl. In particular embodiments, R$^A$ may be H or C$_{1-3}$ alkyl. In particular embodiments, R$^A$ may be H or CH$_3$. In particular embodiments, R$^A$ may be H.

Each R$^B$ may independently be H, or C$_{1-12}$ alkyl, including: linear or branched alkyl having a formula C$_a$H$_{2a+1}$, wherein a is 1, 2, 3, 4, 5, 6, 7, 8, 9, 10, 11, or 12, such as linear or branched alkyl of a formula: CH$_3$, C$_2$H$_5$, C$_3$H, C$_4$H$_9$, C$_5$H$_{11}$, C$_6$H$_{13}$, C$_3$H$_{17}$, C$_7$H$_{15}$, CH$_{19}$, C$_1$H$_{21}$, etc. Each R$^B$ may also be a cycloalkyl having a formula C$_a$H$_a$, wherein a is 3, 4, 5, 6, 7, 8, 9, 10, 11, or 12. In particular embodiments, R$^B$ may be H or C$_{1-3}$ alkyl. In particular embodiments, R$^B$ may be H or CH$_3$. In particular embodiments, R$^B$ may be H.

With respect to any relevant structural representation, such as Formula 2, R$^1$ is H, or any substituent, such as a substituent having a molecular weight of 15 mol/g to 100 mol/g. In particular embodiments, R$^1$ is H, C$_{1-4}$ alkyl, OH, C$_{1-4}$ alkyl-O-alkyl, —CHO, C$_{2-4}$ alkenyl-CO-alkyl, C$_{2-4}$ alkynyl-CO-alkyl, CO$_2$H, C$_{2-4}$ alkenyl-CO$_2$-alkyl, F, Cl, Br, I, NO$_2$, or CN. In particular embodiments, R$^1$ is H. Additionally, for any embodiments wherein R$^1$ is H; R$^2$, R$^3$, R$^4$, R$^5$, R$^6$, R$^7$, R$^8$, R$^9$, R$^{10}$, R$^{11}$, R$^{12}$, R$^{13}$, R$^{14}$, or R$^{15}$, can independently be: R$^A$, F, C, CN, OR$^A$, CF$_3$, NO$_2$, NR$^A$R$^B$, COR$^A$, CO$_2$R$^A$, OCOR$^A$, NR$^A$COR$^B$, or CONR$^A$R$^B$; or H, F, C, CN, CF$_3$, OH, NH$_2$, C$_{1-6}$ alkyl, or C$_{1-6}$ alkoxy. In particular embodiments wherein R$^1$ is H; R$^2$, R$^3$, R$^4$, and R$^{15}$ can independently be H, C$_{1-4}$ alkyl, OH, C$_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, Cl, Br, I, $NO_2$, or CN.

With respect to any relevant structural representation, such as Formula 2, $R^2$ is H, or any substituent, such as a substituent having a molecular weight of 15 mol/g to 100 mol/g. In particular embodiments, $R^2$ is H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, C, Br, I, $NO_2$, or CN. In particular embodiments, $R^2$ is H. Additionally, for any embodiments wherein $R^2$ is H; $R^1$, $R^3$, $R^4$, $R^5$, $R^6$, $R^7$, $R^8$, $R^9$, $R^{10}$, $R^{11}$, $R^{12}$, $R^{13}$, $R^{14}$, or $R^{15}$, can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In particular embodiments wherein $R^2$ is H; $R^1$, $R^3$, $R^4$, and $R^{15}$ can independently be H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, Cl, Br, I, $NO_2$, or CN.

With respect to any relevant structural representation, such as Formula 2, $R^3$ is H, or any substituent, such as a substituent having a molecular weight of 15 mol/g to 100 mol/g. In particular embodiments, $R^3$ is H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, C, Br, I, $NO_2$, or CN. In particular embodiments, $R^3$ is H. Additionally, for any embodiments wherein $R^3$ is H; $R^1$, $R^2$, $R^4$, $R^5$, $R^6$, $R^7$, $R^8$, $R^9$, $R^{10}$, $R^{11}$, $R^{12}$, $R^{13}$, $R^{14}$, or $R^{15}$, can independently be: $R^A$, F, C, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, C, CN, $CF_3$, OH, $NH_2$, $C_{1-6}$ alkyl, or $C_{1-6}$ alkoxy. In particular embodiments wherein $R^3$ is H; $R^1$, $R^2$, $R^4$, and $R^{15}$ can independently be H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, C, Br, I, $NO_2$, or CN.

With respect to any relevant structural representation, such as Formula 2, $R^4$ is H, or any substituent, such as a substituent having a molecular weight of 15 mol/g to 100 mol/g. In particular embodiments, $R^4$ is H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, C, Br, I, $NO_2$, or CN. In particular embodiments, $R^4$ is H. Additionally, for any embodiments wherein $R^4$ is H; $R^1$, $R^2$, $R^3$, $R^5$, $R^6$, $R^7$, $R^8$, $R^9$, $R^{10}$, $R^{11}$, $R^{12}$, $R^{13}$, $R^{14}$, or $R^{15}$, can independently be: $R^A$, F, C, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, C, CN, $CF_3$, OH, $NH_2$, $C_{1-6}$ alkyl, or $C_{1-6}$ alkoxy. In particular embodiments wherein $R^4$ is H; $R^1$, $R^2$, $R^3$, and $R^{15}$ can independently be H, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, Cl, Br, I, $NO_2$, or CN.

With respect to any relevant structural representation, such as Formula 2, $R^5$ is H, or any substituent, such as a substituent having a molecular weight of 15 mol/g to 100 mol/g. In particular embodiments, $R^5$ is H. In particular embodiments, $R^5$ is H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, Cl, Br, I, $NO_2$, or CN. In particular embodiments, $R^5$ is H. Additionally, for any embodiments wherein $R^5$ is H; $R^1$, $R^2$, $R^3$, $R^4$, $R^6$, R, $R^8$, $R^9$, $R^{10}$, $R^{11}$, $R^{12}$, $R^{13}$, $R^{14}$, or $R^{15}$, can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In particular embodiments wherein $R^5$ is H; $R^6$, $R^7$, $R^8$, and $R^9$ can independently be H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, Cl, Br, I, $NO_2$, or CN.

With respect to any relevant structural representation, such as Formula 2, $R^6$ is H, or any substituent, such as a substituent having a molecular weight of 15 mol/g to 100 mol/g. In particular embodiments, $R^6$ is H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, Cl, Br, I, $NO_2$, or CN. In particular embodiments, $R^6$ is H. In particular embodiments, $R^6$ is F. In particular embodiments, $R^6$ is OH. In particular embodiments, $R^6$ is H, F, or OH. Additionally, for any embodiments wherein $R^6$ is H, F, or OH; $R^1$, $R^2$, $R^3$, $R^4$, $R^5$, $R^7$, $R^8$, $R^9$, $R^{10}$, $R^{11}$, $R^{12}$, $R^{13}$, $R^{14}$, or $R^{15}$, can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In particular embodiments wherein $R^6$ is H, F, or OH; $R^5$, $R^7$, $R^8$, and $R^9$ can independently be H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, C, Br, I, $NO_2$, or CN.

With respect to any relevant structural representation, such as Formula 2, $R^7$ is H, or any substituent, such as a substituent having a molecular weight of 15 mol/g to 100 mol/g. In particular embodiments, $R^7$ is H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, C, Br, I, $NO_2$, or CN. In particular embodiments, $R^7$ is H. In particular embodiments, $R^7$ is F. In particular embodiments $R^7$ is OH. In particular embodiments, $R^7$ is H, F, or OH. Additionally, for any embodiments wherein $R^7$ is H, F, or OH; $R^1$, $R^2$, $R^3$, $R^4$, $R^5$, $R^6$, $R^8$, $R^9$, $R^{10}$, $R^{11}$, $R^{12}$, $R^{13}$, $R^{14}$, or $R^{15}$, can independently be: $R^A$, F, C, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, C, CN, $CF_3$, OH, $NH_2$, $C_{1-6}$ alkyl, or $C_{1-6}$ alkoxy. In particular embodiments wherein $R^7$ is H, F, or OH; $R^5$, $R^6$, $R^8$, and $R^9$ can independently be H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, Cl, Br, I, $NO_2$, or CN.

With respect to any relevant structural representation, such as Formula 2, $R^8$ is H, or any substituent, such as a substituent having a molecular weight of 15 mol/g to 100 mol/g. In particular embodiments, $R^8$ is H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, Cl, Br, I, $NO_2$, or CN. In particular embodiments, $R^8$ is H. Additionally, for any embodiments wherein $R^8$ is H; $R^1$, $R^2$, $R^3$, $R^4$, $R^5$, $R^6$, $R^7$, $R^9$, $R^{10}$, $R^{11}$, $R^{12}$, $R^{13}$, $R^{14}$, or $R^{15}$, can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In particular embodiments wherein $R^8$ is H; $R^5$, $R^6$, $R^7$, and $R^9$ can independently be H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, Cl, Br, I, $NO_2$, or CN.

With respect to any relevant structural representation, such as Formula 2, $R^9$ is H, or any substituent, such as a substituent having a molecular weight of 15 mol/g to 100 mol/g. In particular embodiments, $R^9$ is H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, Cl, Br, I, $NO_2$, or CN. In particular embodiments, $R^9$ is H. Additionally, for any embodiments wherein $R^9$ is H; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, or $R^{15}$, can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In particular embodiments wherein $R^9$ is H; $R^5$, $R^6$, $R^7$, and $R^8$ can independently be H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, C, Br, I, $NO_2$, or CN.

With respect to any relevant structural representation, such as Formula 2, $R^{10}$ is H, or any substituent, such as a substituent having a molecular weight of 15 mol/g to 100 mol/g. In particular embodiments, $R^{10}$ is H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, C, Br, I, $NO_2$, or CN. In particular embodiments, $R^{10}$ is H. Additionally, for any embodiments wherein $R^{10}$ is H; $R^1$, $R^2$, $R^3$, $R^4$, $R^5$, $R^6$, $R^7$, $R^8$, $R^9$, $R^{11}$, $R^{12}$, $R^{13}$, $R^{14}$, or $R^{15}$, can independently be: $R^A$, F, C, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In particular embodiments wherein $R^{10}$ is H; $R^{11}$, $R^{12}$, $R^{13}$, and $R^{14}$ can independently be H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, Cl, Br, I, $NO_2$, or CN.

With respect to any relevant structural representation, such as Formula 2, $R^{11}$ is H, or any substituent, such as a substituent having a molecular weight of 15 mol/g to 100 mol/g. In particular embodiments, $R^{11}$ is H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, Cl, Br, I, $NO_2$, or CN. In particular embodiments, $R^{11}$ is H. Additionally, for any embodiments wherein $R^{11}$ is H; $R^1$, $R^2$, $R^3$, $R^4$, $R^5$, $R^6$, $R^7$, $R^8$, $R^9$, $R^{10}$, $R^{12}$, $R^{13}$, $R^{14}$, or $R^{15}$, can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In particular embodiments wherein $R^{11}$ is H; $R^{10}$, $R^{12}$, $R^{13}$, and $R^{14}$ can independently be H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, Cl, Br, I, $NO_2$, or CN.

With respect to any relevant structural representation, such as Formula 2, $R^{12}$ is H, or any substituent, such as a substituent having a molecular weight of 15 mol/g to 100 mol/g. In particular embodiments, $R^{12}$ is H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, Cl, Br, I, $NO_2$, or CN. In particular embodiments, $R^{12}$ is H. Additionally, for any embodiments wherein $R^{12}$ is H; $R^1$, $R^2$, $R^3$, $R^4$, $R^5$, $R^6$, $R^7$, $R^8$, $R^9$, $R^{10}$, $R^{11}$, $R^{13}$, $R^{14}$, or $R^{15}$, can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In particular embodiments wherein $R^{12}$ is H; $R^{10}$, $R^{11}$, $R^{13}$, and $R^{14}$ can independently be H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, Cl, Br, I, $NO_2$, or CN.

With respect to any relevant structural representation, such as Formula 2, $R^{13}$ is H, or any substituent, such as a substituent having a molecular weight of 15 mol/g to 100 mol/g. In particular embodiments, $R^{13}$ is H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, C, Br, I, $NO_2$, or CN. In particular embodiments, $R^{13}$ is H. Additionally, for any embodiments wherein $R^{13}$ is H; $R^1$, $R^2$, $R^3$, $R^4$, $R^5$, $R^6$, $R^7$, $R^8$, $R^9$, $R^{10}$, $R^{11}$, $R^{12}$, $R^{14}$, or $R^{15}$, can independently be: $R^A$, F, C, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, C, CN, $CF_3$, OH, $NH_2$, $C_{1-6}$ alkyl, or $C_{1-6}$ alkoxy. In particular embodiments wherein $R^{13}$ is H; $R^{10}$, $R^{11}$, $R^{12}$, and $R^{14}$ can independently be H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, C, Br, I, $NO_2$, or CN.

With respect to any relevant structural representation, such as Formula 2, $R^{14}$ is H, or any substituent, such as a substituent having a molecular weight of 15 mol/g to 100 mol/g. In particular embodiments, $R^{14}$ is H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, Cl, Br, I, $NO_2$, or CN. In particular embodiments, $R^{14}$ is H. In particular embodiments $R^{14}$ is $CH_3$. In particular embodiments, $R^{14}$ is H or $CH^3$. Additionally, for any embodiments wherein $R^{14}$ is H or $CH_3$; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, or $R^{15}$, can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In particular embodiments wherein $R^{14}$ is H or $CH_3$; $R^{10}$, $R^{11}$, $R^{12}$, and $R^{13}$ can independently be H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, Cl, Br, I, $NO_2$, or CN.

With respect to any relevant structural representation, such as Formula 2, $R^{15}$ is H, or any substituent, such as a substituent having a molecular weight of 15 mol/g to 100 mol/g. In particular embodiments, $R^{15}$ is H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, Cl, Br, I, $NO_2$, or CN. In particular embodiments, $R^{15}$ is H. In particular embodiments $R^{15}$ is $CH_3$. In particular embodiments, $R^{15}$ is H or $CH_3$. Additionally, for any embodiments wherein $R^{15}$ is H or $CH_3$; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, or $R^{15}$, can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In particular embodiments wherein $R^{15}$ is H or $CH_3$; $R^1$, $R^2$, $R^3$, and $R^4$ can independently be H, $C_{1-4}$ alkyl, OH, $C_{1-4}$ alkyl-O-alkyl, —CHO, $C_{2-4}$ alkenyl-CO-alkyl, $C_{2-4}$ alkynyl-CO-alkyl, $CO_2H$, $C_{2-4}$ alkenyl-$CO_2$-alkyl, F, C, Br, I, $NO_2$, or CN.

With respect to any relevant structural representation, such as Formula 2, in particular embodiments R7 and R8 are F. In particular embodiments R7 and R8 are OH. In particular embodiments, R14 and R15 are CH3. In particular embodiments, R5 and R9 are H. In particular embodiments, R6 and R9 are H. In particular embodiments, R5, R6, and R9 are H.

Particular Exemplary Compounds Include:

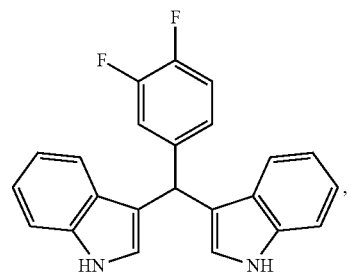

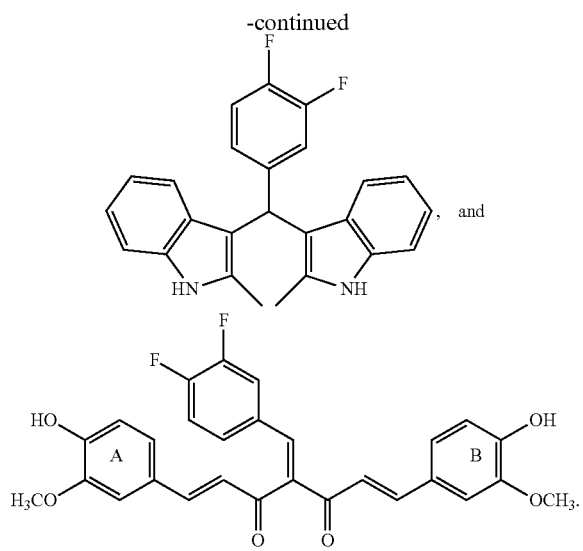
, and

Pharmaceutical compositions can be formed by combining a compound disclosed herein, or a pharmaceutically acceptable prodrug or salt thereof, with a pharmaceutically acceptable carrier suitable for delivery to a subject in accordance with known methods of drug delivery. Compounds can also be provided as alternate solid forms, such as polymorphs, solvates, hydrates, etc.; tautomers; or any other chemical species that may rapidly convert to a compound described herein under conditions in which the compounds are used as described herein.

As used herein, the term "pharmaceutically acceptable salt" refers to pharmaceutical salts that are, within the scope of sound medical judgment, suitable for use in contact with the tissues of subjects without undue toxicity, irritation, and allergic response, and are commensurate with a reasonable benefit/risk ratio. Pharmaceutically acceptable salts are well known in the art. In one embodiment, the pharmaceutically acceptable salt is a sulfate salt. For example, S. M. Berge, et al. describes pharmaceutically acceptable salts in J. Pharm. Sci., 1977, 66:1-19.

Suitable pharmaceutically acceptable acid addition salts can be prepared from an inorganic acid or an organic acid. Examples of such inorganic acids are hydrochloric, hydrobromic, hydroiodic, nitric, carbonic, sulfuric, and phosphoric acid. Appropriate organic acids can be selected from aliphatic, cycloaliphatic, aromatic, arylaliphatic, heterocyclic, carboxylic and sulfonic classes of organic acids, examples of which are formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, p-hydroxybutyric, malonic, galactic, and galacturonic acid. Pharmaceutically acceptable acidic/anionic salts also include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, polygalacturonate, salicylate, stearate, subacetate, succinate, sulfate, hydrogensulfate, tannate, tartrate, teoclate, tosylate, and triethiodide salts.

Suitable pharmaceutically acceptable base addition salts include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, lysine, arginine and procaine. All of these salts can be prepared by conventional means from the corresponding compound represented by the disclosed compounds by treating, for example, the disclosed compounds with the appropriate acid or base. Pharmaceutically acceptable basic/cationic salts also include, the diethanolamine, ammonium, ethanolamine, piperazine and triethanolamine salts.

A pharmaceutically acceptable salt includes any salt that retains the activity of the parent compound and is acceptable for pharmaceutical use. A pharmaceutically acceptable salt also refers to any salt which may form in vivo as a result of administration of an acid, another salt, or a prodrug which is converted into an acid or salt.

A prodrug includes a compound which is converted to a therapeutically active compound after administration, such as by hydrolysis of an ester group or some other biologically labile group.

The compounds disclosed herein can be provided as part of pharmaceutical compositions that include a compound disclosed herein and at least one pharmaceutically acceptable excipient.

In particular embodiments, the compounds are provided as part of a composition that can include, for example, at least 0.1% w/v of compound(s); at least 1% w/v of compound(s); at least 10% w/v of compound(s); at least 20% w/v of compound(s); at least 30% w/v of compound(s); at least 40% w/v of compound(s); at least 50% w/v of compound(s); at least 60% w/v of compound(s); at least 70% w/v of compound(s); at least 80% w/v of compound(s); at least 90% w/v of compound(s); at least 95% w/v of compound(s); or at least 99% w/v of compound(s).

In other embodiments, the active ingredients are provided as part of a composition that can include, for example, at least 0.1% w/w of compound(s); at least 1% w/w of compound(s); at least 10% w/w of compound(s); at least 20% w/w of compound(s); at least 30% w/w of compound(s); at least 40% w/w of compound(s); at least 50% w/w of compound(s); at least 60% w/w of compound(s); at least 70% w/w of compound(s); at least 80% w/w of compound(s); at least 90% w/w of compound(s); at least 95% w/w of compound(s); or at least 99% w/w of compound(s).

The compounds and pharmaceutical compositions disclosed herein can be formulated for administration by, without limitation, injection, inhalation, infusion, perfusion, lavage or ingestion. The compositions disclosed herein can further be formulated for, without limitation, intravenous, intradermal, intraarterial, intranodal, intralymphatic, intraperitoneal, intralesional, intraprostatic, intravaginal, intrarectal, topical, intrathecal, intratumoral, intramuscular, intravesicular, oral and/or subcutaneous administration and more particularly by intravenous, intradermal, intraarterial, intranodal, intralymphatic, intraperitoneal, intralesional, intraprostatic, intravaginal, intrarectal, topical, intrathecal, intratumoral, intramuscular, intravesicular, oral and/or subcutaneous injection.

For injection, compositions can be formulated as aqueous solutions, such as in buffers including Hanks' solution, Ringer's solution, or physiological saline. The aqueous solutions can contain formulatory agents such as suspending, stabilizing and/or dispersing agents. Alternatively, the formulation can be in lyophilized and/or powder form for constitution with a suitable vehicle, e.g., sterile pyrogen-free water, before use.

For oral administration, the compositions can be formulated as tablets, pills, dragees, capsules, liquids, gels, syrups, slurries, suspensions and the like. For oral solid formulations such as, for example, powders, capsules and tablets, suitable excipients include binders (gum tragacanth, acacia, cornstarch, gelatin), fillers such as sugars, e.g. lactose, sucrose, mannitol and sorbitol; dicalcium phosphate, starch, magnesium stearate, sodium saccharine, cellulose, magnesium carbonate; cellulose preparations such as maize starch, wheat starch, rice starch, potato starch, gelatin, gum tragacanth, methyl cellulose, hydroxypropylmethyl-cellulose, sodium carboxy-methylcellulose, and/or polyvinylpyrrolidone (PVP); granulating agents; and binding agents. If desired, disintegrating agents can be added, such as corn starch, potato starch, alginic acid, cross-linked polyvinylpyrrolidone, agar, or alginic acid or a salt thereof such as sodium alginate. If desired, solid dosage forms can be sugar-coated or enteric-coated using standard techniques. Flavoring agents, such as peppermint, oil of wintergreen, cherry flavoring, orange flavoring, etc. can also be used.

Compositions including a compound disclosed herein can be administered as an aerosol for the treatment of pneumonia or other lung-based infections. In one embodiment, the aerosol delivery vehicle is an anhydrous, liquid or dry powder inhaler. A compound of Formula 1, Formula 2, or Formula 3 can be included in a pharmaceutical composition formulated for delivery as a dry powder or aerosol for nasal, sinunasal or pulmonary administration in a manner suitable for the prevention, management or treatment of airway infections.

For administration by inhalation, compositions can be formulated as aerosol sprays from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

Any composition formulation disclosed herein can advantageously include any other pharmaceutically acceptable carriers which include those that do not produce significantly adverse, allergic or other untoward reactions that outweigh the benefit of administration, whether for research, prophylactic and/or therapeutic treatments. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety and purity standards as required by US FDA Office of Biological Standards and/or other relevant foreign regulatory agencies.

Exemplary generally used pharmaceutically acceptable carriers include any and all bulking agents or fillers, solvents or co-solvents, dispersion media, coatings, surfactants, antioxidants (e.g., ascorbic acid, methionine, vitamin E), preservatives, isotonic agents, absorption delaying agents, salts, stabilizers, buffering agents, chelating agents (e.g., EDTA), gels, binders, disintegration agents, and/or lubricants.

Exemplary buffering agents include citrate buffers, succinate buffers, tartrate buffers, fumarate buffers, gluconate buffers, oxalate buffers, lactate buffers, acetate buffers, phosphate buffers, histidine buffers and/or trimethylamine salts.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol and 3-pentanol.

Exemplary isotonic agents include polyhydric sugar alcohols including trihydric or higher sugar alcohols, such as glycerin, erythritol, arabitol, xylitol, sorbitol or mannitol.

Exemplary stabilizers include organic sugars, polyhydric sugar alcohols, polyethylene glycol; sulfur-containing reducing agents, amino acids, low molecular weight polypeptides, proteins, immunoglobulins, hydrophilic polymers or polysaccharides.

Compounds can also be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salts.

Additionally, compositions can be formulated as sustained-release systems utilizing semipermeable matrices of solid polymers containing at least one compound. Various sustained-release materials have been established and are well known by those of ordinary skill in the art. Sustained-release systems may, depending on their chemical nature, release active ingredients following administration for a few weeks up to over 100 days.

The compounds can be in powder or lyophilized form for reconstitution in the appropriate pharmaceutically acceptable carrier at the time of delivery. In another embodiment, the unit dosage form of the compound can be a solution of the antibacterial compound of Formula 1, Formula 2, or Formula 3 or a pharmaceutically acceptable salt thereof, in a suitable diluent in sterile, hermetically sealed ampoules or sterile syringes.

Methods disclosed herein include treating subjects (humans, veterinary animals, livestock and research animals) with compounds disclosed herein including salts and prodrugs thereof. Treating subjects can include delivering an effective amount and/or delivering a prophylactic treatment and/or a therapeutic treatment. An "effective amount" is the amount of a compound necessary to result in a desired physiological change in the subject. Effective amounts are often administered for research purposes. Effective amounts disclosed herein reduce, control, or eliminate the presence or activity of unwanted bacteria and/or reduce control or eliminate unwanted side effects of unwanted bacteria.

A "prophylactic treatment" includes a treatment administered to a subject who does not display signs or symptoms of a bacterial infection or displays only early signs or symptoms of the bacterial infection such that treatment is administered for the purpose of diminishing, preventing, or decreasing the risk of developing the bacterial infection further. Thus, a prophylactic treatment functions as a preventative treatment against a bacterial infection.

A "therapeutic treatment" includes a treatment administered to a subject who displays symptoms or signs of a bacterial infection and is administered to the subject for the purpose of diminishing or eliminating those signs or symptoms of the bacterial infection. The therapeutic treatment can reduce, control, or eliminate the presence or activity of unwanted bacteria and/or reduce control or eliminate unwanted side effects of unwanted bacteria.

"Therapeutically effective amounts" include those that provide effective amounts, prophylactic treatments and/or therapeutic treatments. Therapeutically effective amounts need not fully prevent or cure the disease or condition but can also provide a partial benefit, such as reduction in the presence and/or activity and/or side effects of the unwanted bacteria.

For administration, therapeutically effective amounts (also referred to herein as doses) can be initially estimated based on results from in vitro assays and/or animal model studies. For example, a dose can be formulated in animal models to achieve a circulating concentration range that includes an IC50 as determined in cell culture against a particular target. Such information can be used to more accurately determine useful doses in subjects of interest.

The actual dose amount administered to a particular subject can be determined by a physician, veterinarian or researcher taking into account parameters such as physical and physiological factors including target, body weight, severity of condition, type of bacterial infection, previous or concurrent therapeutic interventions, idiopathy of the subject and route of administration.

The amount and concentration of antibacterial compound in a pharmaceutical composition, as well as the quantity of the pharmaceutical composition administered to a subject, can be selected based on clinically relevant factors, the solubility of the antibacterial compound in the pharmaceutical composition, the potency and activity of the antibacterial compound, and the manner of administration of the pharmaceutical composition. A pharmaceutical composition including a therapeutically effective amount of an antibacterial compound of Formula 1, Formula 2, or Formula 3 or a pharmaceutically acceptable salt or prodrug thereof, can be administered intravenously to a patient for treatment of bacterial infections in a clinically safe and effective manner, including one or more separate administrations of the composition. For example, 0.05 mg/kg to 5.0 mg/kg can be administered to a subject per day in one or more doses (e.g., doses of 0.05 mg/kg QD, 0.10 mg/kg QD, 0.50 mg/kg QD, 1.0 mg/kg QD, 1.5 mg/kg QD, 2.0 mg/kg QD, 2.5 mg/kg QD, 3.0 mg/kg QD, 0.75 mg/kg BID, 1.5 mg/kg BID or 2.0 mg/kg BID). For certain antibiotic indications, the total daily dose of a compound of Formula 1, Formula 2, or Formula 3 can be 0.05 mg/kg to 3.0 mg/kg of administered intravenously to a subject one to three times a day, including administration of total daily doses of 0.05-3.0, 0.1-3.0, 0.5-3.0, 1.0-3.0, 1.5-3.0, 2.0-3.0, 2.5-3.0, and 0.5-3.0 mg/kg/day of a compounds of Table 1 using 60-minute QD, BID or TID intravenous infusion dosing. In one particular example, antibiotic pharmaceutical compositions can be intravenously administered QD or BID to a subject with, e.g., total daily doses of 1.5 mg/kg, 3.0 mg/kg, 4.0 mg/kg of a composition with up to 92-98% wt/wt of a compound of Formula 1, Formula 2, or Formula 3. The amount per administered dose and the total amount administered will depend on factors such as the nature and severity of the infection, the age and general health of the patient, the tolerance of the patient to the compound and the microorganism or microorganisms involved in the infection.

Additional useful doses can often range from 0.1 to 5 µg/kg or from 0.5 to 1 µg/kg. In other non-limiting examples, a dose can include 1 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 1000 µg/kg, 0.1 to 5 mg/kg or from 0.5 to 1 mg/kg.

In other non-limiting examples, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg or more.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months or yearly.

The antibacterial compounds of Formula 1, Formula 2, or Formula 3 can be used in vivo, for example, to treat bacterial infections in a subject, as well as in vitro, for example to treat cells (e.g., bacteria) in culture to eliminate or reduce the level of bacterial contamination of a cell culture. In one embodiment, a compound of Formula 1, Formula 2, or Formula 3, or a composition thereof, is administered to a cell culture, such as by administering in a nutrient medium. Compounds disclosed herein can also be used as disinfectants.

Methods of treatment of such infections include administering to a subject in need thereof a therapeutically effective amount of an antibacterial compound of Formula 1, Formula 2, or Formula 3. The compound can be parenterally administered to a subject having or suspected to have a bacterial infection.

The antibacterial compounds of Formula 1. Formula 2, or Formula 3 are used in vivo to treat an infection in a subject by administering a therapeutically effective amount of a compound of Formula 1, Formula 2, or Formula 3, or a pharmaceutically acceptable salt or prodrug thereof, in a pharmaceutical composition. The method can include parenterally administering to a subject in need thereof a pharmaceutical composition including a compound of Formula 1, Formula 2, or Formula 3, or a pharmaceutically acceptable salt or prodrug thereof. Pharmaceutical compositions include compositions including a compound of Formula 1, Formula 2, or Formula 3 in an amount sufficient to achieve the intended purpose, i.e., the treatment or prevention of a bacterial infection.

In particular, the pharmaceutical compositions including antibacterial compound of Formula 1, Formula 2, or Formula 3 can be used to treat a subject having a bacterial infection. The compounds of Formula 1, Formula 2, and Formula 3 have broad spectrum antibacterial activity. The compounds can be used to treat bacterial infection caused by one or more Gram-negative and/or Gram-positive bacteria. Exemplary Gram-negative bacteria include species of *Acinetobacter, Citrobacter, Enterobacter, Escherichia, Pseudomonas, Kebsiella, Salmonella, Shigella, Yersinia, Pasteurella, Brucella, Bordetella, Proteus, Serratia, Providencia, Helicobacter, Moraxella, Stenotrophomonas, Bdellovibrae, Vibrio, Legionella, Neisseria*, and *Edwardsiella*. In one embodiment, the compounds of Table 1 may be used to treat MDR Gram-negative bacteria, such as MDR *P. aeruginosa*, Extended Spectrum Beta Lactamase (ESBL) *K. pneumonia*, ESBL *E. coli*, and *A. baumannii*. Exemplary Gram-positive bacteria include species of *Streptococcus, Staphylococcus, Corynebacterium, Listeria, Bacillus, Enterococcus*, and *Clostridium*. In one embodiment, the compounds of Table 1 may be used to treat MDR Gram-positive bacteria, such as MRSA. In another embodiment, the compounds of Table 1 may be used to treat vancomycin-resistant Enterococci.

Further disclosed is the use of a synergistic effect of a compound of Formula 1, Formula 2, or Formula 3 in combination with another compound of Formula 1, Formula 2, or Formula 3 and/or another anti-bacterial agent. In particular embodiments, the compounds of Formula 1, Formula 2, or Formula 3 are used for the purpose of plasmid curing. Following, or in conjunction with plasmid curing, one or more additional antibacterial agents with a different antibacterial mechanism of action can be administered (see, for example, FIG. 1A). Exemplary antibacterial agents include aminoglycosides (e.g., amikacin, gentamicin, kanamycin, neomycin, netilmicin, tobramycin, paromomycin, spectinomycin), ansamycins (e.g., geldanomycin, herbimycin, rifaximin, streptomycin), carbacephems (e.g., loracarbef), carbapenems (e.g., ertapenem, doripenem, imipenem, cilastatin, meropenem), cephalosporins (e.g., cefadroxil, cefazolin, cefalotin or cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole), glycopeptides (e.g., teicoplanin, vancomycin, telavancin), lincosamides (e.g., clindamycin, lincomycin), lipopeptides (e.g., daptomycin), macrolides (e.g., azithromycin, clarithromycin, dirithromycin, erythromycin, roxithromycin, troleandomycin, telithromycin, spiramycin), monobactams (e.g., aztreonam), nitrofurans (e.g., furazolidone, nitrofurantoin), oxazolidonones (e.g., linezolid, posizolid, radezolid, torezolid), penicillins (e.g., amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, penicillin G, temocillin, ticarcillin), penicillin combinations (e.g., amoxicillin/clavulanate, ampicillin/sulbactam, piperacillin/tazobactam, ticarcillin/clavulanate), polypeptides (e.g., bacitracin, colistin, polymyxin B), quinolones (e.g., ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin), sulfonamides (e.g., mafenide, sulfacetamide, sulfadiazine, silver sulfadiazine, sulfadimethoxine, sulfamethizole, sulfamethoxazole, sulfanilimide (archaic), sulfasalazine, sulfisoxazole, trimethoprim-, sulfamethoxazole (co-trimoxazole) (TMP-SMX), sulfonamidochrysoidine), tetracyclines (e.g., demeclocycline, doxycycline, minocycline, oxytetracycline, tetracycline), and others (e.g., clofazimine, dapsone, capreomycin, cycloserine, ethambutol, ethionamide, isoniazid, pyrazinamide, rifampicin (rifampin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, trimethoprim).

The Exemplary Embodiments and Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

EXEMPLARY EMBODIMENTS

1. A compound represented by Formula 1:

wherein Ph is optionally substituted phenyl; and Het is optionally substituted indolyl; and $Het^2$ is optionally substituted indolyl.

2. A compound of embodiment 1, further represented by a Formula 2:

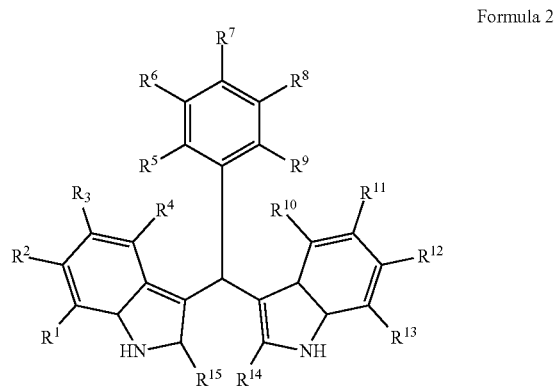

wherein $R^1$-$R^{15}$ can independently be H, F, Cl, Br, I, or $NO_2$, $C_{1-6}$ alkyl, $C_{1-6}$ hydroxyalkyl, or optionally substituted phenyl.

3. A compound of embodiment 1, wherein Ph is dihydroxyphenyl.

4. A compound of embodiment 1, wherein Ph is difluorophenyl.

5. A compound of embodiment 1, wherein Het is unsubstituted indol-3-yl.

6. A compound of embodiment 1, wherein $Het^2$ is unsubstituted indol-3-yl.

7. A compound of embodiment 1, wherein $Het^1$ has a $CH_3$ substituent.

8. A compound of embodiment 1, wherein $Het^2$ has a $CH_3$ substituent.

9. A compound of embodiment 1, wherein the compound is HN18 or HN34.

10. A pharmaceutical composition including a compound of any one of claims 1-9; a pharmaceutically acceptable salt of any one of embodiments 1-9; or a pharmaceutically acceptable prodrug of any one of the compounds of embodiments 1-9; and at least one pharmaceutically acceptable excipient.

11. A pharmaceutical composition of embodiment 10, wherein the compound is:

12. A pharmaceutical composition of embodiment 10, wherein the compound is:

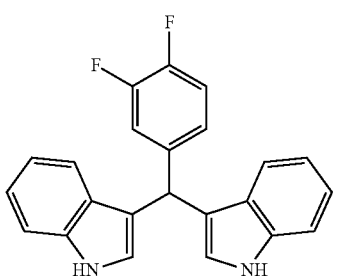 [SMILES: Fc1ccc(C(c2c[nH]c3ccccc23)c2c[nH]c3ccccc23)cc1F]

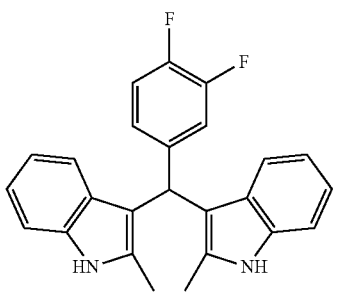 [SMILES: Cc1[nH]c2ccccc2c1C(c1ccc(F)c(F)c1)c1c(C)[nH]c2ccccc12]

13. A method of treating a bacterial infection in a subject in need thereof including administering a therapeutically effective amount of a compound of any one of claims 1-9 or a pharmaceutical composition of any one of embodiments 10-12 to the subject, thereby treating the bacterial infection in the subject.
14. A method of embodiment 13, further including administering an additional antibacterial agent selected from one or more of an aminoglycoside, an ansamycin, a carbacephem, a carbapenem, a cephalosporin, a glycopeptide, a lincosamide, a lipopeptide, a macrolide, a monobactam, a nitrofuran, an oxazolidonone, a penicillin, a penicillin combination, a quinolone, a sulfonamide, a tetracycline, and a combination thereof.
15. A method of embodiment 14 wherein the aminoglycoside is selected from one or more of amikacin, gentamicin, kanamycin, neomycin, netilmicin, tobramycin, paromomycin, and spectinomycin.
16. A method of embodiment 14 wherein the ansamycin is selected from one or more of geldanomycin, herbimycin, rifaximin, and streptomycin.
17. A method of embodiment 14 wherein the carbacephem is loracarbef.
18. A method of embodiment 14 wherein the carbapenem is selected from one or more of ertapenem, doripenem, imipenem, cilastatin, and meropenem.
19. A method of embodiment 14 wherein the cephalosporin is selected from one or more of cefadroxil, cefazolin, cefalotin or cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, and ceftobiprole.
20. A method of embodiment 14 wherein the glycopeptide is selected from one or more of teicoplanin, vancomycin, and telavancin.
21. A method of embodiment 14 wherein the lincosamide is selected from one or more of clindamycin, and lincomycin.
22. A method of embodiment 14 wherein the lipopeptide is daptomycin.
23. A method of embodiment 14 wherein the macrolide is selected from one or more of azithromycin, clarithromycin, dirithromycin, erythromycin, roxithromycin, troleandomycin, telithromycin, and spiramycin.
24. A method of embodiment 14 wherein the monobactam is aztreonam.
25. A method of embodiment 14 wherein the nitrofuran is selected from one or more of furazolidone, and nitrofurantoin.
26. A method of embodiment 14 wherein the oxazolidonone is selected from one or more of linezolid, posizolid, radezolid, and torezolid.
27. A method of embodiment 14 wherein the penicillin is selected from one or more of amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, penicillin G, temocillin, and ticarcillin.
28. A method of embodiment 14 wherein the penicillin combination is selected from one or more of amoxicillin/clavulanate, ampicillin/sulbactam, piperacillin/tazobactam, and ticarcillin/clavulanate.
29. A method of embodiment 14 wherein the quinolone is selected from one or more of ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, and temafloxacin.
30. A method of embodiment 14 wherein the sulfonamide is selected from one or more of mafenide, sulfacetamide, sulfadiazine, silver sulfadiazine, sulfadimethoxine, sulfamethizole, sulfamethoxazole, sulfanilimide (archaic), sulfasalazine, sulfisoxazole, trimethoprim, sulfamethoxazole (co-trimoxazole) (TMP-SMX), and sulfonamidochrysoidine.
31. A method of embodiment 14 wherein the tetracycline is selected from one or more of demeclocycline, doxycycline, minocycline, oxytetracycline, and tetracycline.
32. A method of embodiment 13, further including administering an antibacterial agent selected from one or more of clofazimine, dapsone, capreomycin, cycloserine, ethambutol, ethionamide, isoniazid, pyrazinamide, rifampicin (rifampin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, and trimethoprim.
33. A method of any one of embodiments 13-32 wherein the bacterial infection is caused by a gram-negative and/or a gram-positive bacterium.
34. A method of any one of embodiments 13-32 wherein the bacterial infection is caused by a bacterial species selected from one or more of *Acinetobacter, Bordetella, Brucella, Citrobacter, Edwardsiella, Enterobacter, Escherichia, Helicobacter, Klebsiella, Moraxella, Legionella, Neisseria, Pasteurella, Proteus, Providencia, Pseudomonas, Salmonella, Serratia, Shigella, Stenotrophomonas, Vibrio*, and *Yersinia*.
35. A method of any one of embodiments 13-32 wherein the bacterial infection is caused by a multiple drug resistant (MDR) Gram-negative bacterium.
36. A method of embodiment 34 wherein the MDR Gram-negative bacteria is caused by one or more of *P. aeruginosa*, Extended Spectrum Beta Lactamase (ESBL) *K. pneumonia*, ESBL *E. coli*, and *A. baumannii*.
37. A method of any one of embodiments 13-32 wherein the bacterial infection is caused by a Gram-positive bacterial species selected from one or more of *Streptococcus, Staphylococcus, Enterococcus, Corynebacterium, Listeria, Bacillus,* and *Clostridium.*

38. A method of any one of embodiments 13-32 wherein the bacterial infection is caused by an MDR Gram-positive bacterium.

39. A method of any one of embodiments 13-32 wherein the bacterial infection is caused by methicillin-resistant *S. aureus* or vancomycin-resistant Enterococci.

40. A method of plasmid curing a bacterium including contacting the bacterium with a therapeutically effective amount of a compound of any one of embodiments 1-9 or a pharmaceutical composition of any one of embodiments 10-12 thereby plasmid curing the bacterium.

41. A method of embodiment 40 wherein the plasmid curing occurs in vitro.

42. A method of embodiment 40 wherein the plasmid curing occurs in vivo.

43. A method of embodiment 40 wherein the plasmid curing occurs in vivo in a subject.

44. A method of embodiment 41 wherein the subject is suffering from a bacterial infection.

45. A method of any one of embodiments 40-44 wherein the bacterium is a Gram-negative bacterium or a Gram-positive bacterium.

46. A method of any one of embodiments 40-44 wherein the plasmid is an antibiotic resistance plasmid.

47. A method of treating a bacterial infection in a subject including administering a therapeutically effective amount of HN18 and oxacillin to the subject, thereby treating the bacterial infection in the subject.

48. A method of treating a bacterial infection in a subject in need thereof including administering a therapeutically effective amount of HN19 or a pharmaceutical composition including HN19 to the subject, thereby treating the bacterial infection in the subject.

49. A method of embodiment 48, further including administering an additional antibacterial agent selected from one or more of an aminoglycoside, an ansamycin, a carbacephem, a carbapenem, a cephalosporin, a glycopeptide, a lincosamide, a lipopeptide, a macrolide, a monobactam, a nitrofuran, an oxazolidonone, a penicillin, a penicillin combination, a quinolone, a sulfonamide, a tetracycline, and a combination thereof.

50. A method of embodiment 48, further including administering an antibacterial agent selected from one or more of clofazimine, dapsone, capreomycin, cycloserine, ethambutol, ethionamide, isoniazid, pyrazinamide, rifampicin (rifampin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, and trimethoprim.

51. A method of any one of embodiments 48-51 wherein the bacterial infection is caused by a gram-negative and/or a gram-positive bacterium.

52. A method of plasmid curing a bacterium including contacting the bacterium with a therapeutically effective amount of HN19 or a pharmaceutical composition including HN19, thereby plasmid curing the bacterium.

EXAMPLES

Example 1. Test Compounds

Compounds were tested for their anti-bacterial activity against 56 clinical isolates including 24 clinical isolates of methicillin resistant *S. aureus* (MRSA) and methicillin-susceptible *S. aureus* (MSSA), 8 strains of *Enterococcus,* 8 strains of *Acinetobacter baumannii,* 8 strains of *Kiebsiella pneumoniae,* and 8 strains of *Pseudomonas aeruginosa* using a standard broth micro-dilution method as recommended by the Clinical and Laboratory Standard Institute (CLSI, M100, s23).

The following three compounds, HN18, HN19, and HN34, were selected for further study:

TABLE 1

| Compound | Structure |
|---|---|
| HN18 | 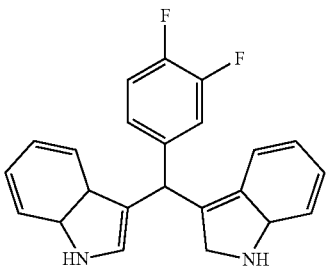 [SMILES: Fc1ccc(C(C2=CNC3C=CC=CC23)C2=C3C=CC=CC3NC2)cc1F]<br>DIM-DF<br>$C_{23}H_{16}F_2N_2$<br>Mol. Wt.: 358.38<br>3-((3,4-difluorophenyl)(2,7a-dihydro-1H-indol-3-yl)methyl)-3a,7a-dihydro-1H-indole |

TABLE 1-continued

| Compound | Structure |
|---|---|
| HN19 | CDF (Curcumin-difluorinated)<br>$C_{28}H_{22}F_2O_6$<br>Mol. Wt.: 492.14<br>(1E,6E)-1,7-bis(4-hydroxy-3-methoxyphenyl)hepta-1,6-diene{4(3,4 difluorobenzylidene)}-3,5-dione (HN19) |
| HN34 | MeDIM-DF<br>$C_{25}H_{20}F_2N_2$<br>Mol. Wt.: 386.44<br>3-((3,4-difluorophenyl)(2-methyl-2,7a-dihydro-1H-indol-3-yl)methyl)-2-methyl-3a,7a-dihydro-1H-indole |

Synthesis of 3-((3,4-difluorophenyl)(2,7a-dihydro-1H-indol-3-yl)methyl)-3a,7a-dihydro-1H-indole (HN18). Indole (586 mg, 5.0 mmol) was suspended in water (25 mL) and 3,4-difluorobenzaldehyde (276 μL, 2.5 mmol) was added. A catalytic amount of concentrated sulfuric acid (3 drops) was added to the mixture before stirring at 90° C. for 1.5 hour. Ethyl acetate was added to dissolve the precipitate. The organic phase was separated, dried over $Na_2SO_4$, filtered, and the filtrate was concentrated in vacuum. The residue thus obtained was purified by column chromatography (silica gel 60). Yield: 750 mg (84%); off-white solid of m.p. 93-95° C.; $v_{max}$ (ATR)/cm$^{-1}$ 3403, 1607, 1509, 1455, 1429, 1417, 1337, 1273, 1202, 1110, 1092, 1038, 1009, 946, 883, 874, 787, 768, 740; $^1$H NMR (300 MHz, CDCl$_3$) δ 5.85 (1H, s), 6.5-6.6 (2H, m), 7.0-7.3 (7H, m), 7.3-7.4 (4H, m), 7.78 (2H, s); $^{13}$C NMR (75.5 MHz, CDCl$_3$) δ 39.4, 111.2, 116.6, 116.8, 117.3, 117.5, 118.8, 119.4, 119.6, 122.1, 124.2, 124.4, 126.7, 136.6, 141.1, 141.2, 147.1, 147.3, 148.5, 148.6, 150.4, 150.5, 151.7, 151.9; MS (EI) m/z 358 [M$^+$] (100%), 245 (62), 122 (25).

Synthesis of 3-((3,4-difluorophenyl)(2-methyl-2,7a-dihydro-1H-indol-3-yl)methyl)-2-methyl-3a,7a-dihydro-1H-indole (HN34). Compound HN34 (775 mg, 2.01 mmol, 80%) was synthesized in a similar manner as HN18. Compound HN34 was obtained from 2-methylindole (656 mg, 5.0 mmol) and 3,4-difluorobenzaldehyde (276 μL, 2.5 mmol); off-white solid of m.p. 222-225° C.; $v_{max}$ (ATR)/cm$^{-1}$ 3383, 3055, 2916, 1606, 1511, 1460, 1428, 1339, 1302, 1278, 1244, 1201, 1109, 1016, 928, 863, 823, 766, 741; $^1$H NMR (300 MHz, CDCl$_3$) δ 2.01 (6H, s), 5.89 (1H, s), 6.7-6.8 (2H, m), 6.8-7.0 (7H, m), 7.20 (2H, d, J=8.1 Hz); $^{13}$C NMR (75.5 MHz, DMSO-d$_6$) δ 11.8, 37.8, 110.4, 111.4, 116.7, 116.9, 117.1, 117.3, 118.1, 118.2, 119.6, 125.1, 127.9, 132.3, 135.1, 142.3, 145.9, 146.1, 147.4, 147.6, 149.3, 150.7, 150.8; MS (EI) m/z 386 [M$^+$] (81%), 371 (70), 254 (100), 162 (68), 120 (67), 44 (70).

Synthesis of (1E,6E)-1,7-bis(4-hydroxy-3-methoxyphenyl)hepta-1,6-diene{4(3,4 difluorobenzylidene)}-3,5-dione (HN19). The synthesis of HN19 is described in WO 2011/142795 and US 2014/0303109.

Example 2. Effects of Test Compounds on MRSA and MSSA Isolates

HN18 HN19, and HN34 were tested by a broth microdilution method to determine their minimal inhibitory concentration (MIC) against 24 strains of *S. aureus* (SA1-SA24) (Table 2). All three compounds were effective against the panel of *S. aureus* strains. Furthermore, the results for HN18 and HN34 were consistent across four repeated experiments. HN18 and HN34 showed higher antibacterial activity as indicated by their lower MIC values.

TABLE 2

| | Compound MIC (μg/ml) | | | | | | | | | | | |
|---|---|---|---|---|---|---|---|---|---|---|---|---|
| Iso- | HN18 | | | | HN19 | | | | HN34 | | | |
| late | I | II | III | IV | I | II | III | IV | I | II | III | IV |
| SA1 | 0.5 | 1 | | 1 | 1 | 8 | 8 | 16 | 1 | 2 | 1 | 1 |
| SA2 | 1 | 2 | 2 | 2 | 1 | 4 | 4 | 8 | 2 | 2 | 1 | 1 |
| SA3 | 1 | 2 | 2 | 2 | 1 | 4 | 8 | 8 | 2 | 2 | 2 | 2 |
| SA4 | 1 | 2 | 1 | 2 | | 2 | 4 | 8 | 1 | 2 | 2 | 2 |

TABLE 2-continued

| | Compound MIC (μg/ml) | | | | | | | | | | | |
|---|---|---|---|---|---|---|---|---|---|---|---|---|
| Iso- | HN18 | | | | HN19 | | | | HN34 | | | |
| late | I | II | III | IV | I | II | III | IV | I | II | III | IV |
| SA5 | 1 | 1 | 1 | 2 | 0.5 | 2 | 4 | 8 | 1 | 2 | 1 | 2 |
| SA6 | 1 | 2 | 2 | 2 | 0.5 | 4 | 4 | 8 | 1 | 1 | 1 | 1 |
| SA7 | 0.5 | 1 | 1 | 1 | 0.5 | 4 | 4 | 8 | 1 | 1 | 1 | 1 |
| SA8 | 1 | 2 | 2 | 2 | 0.5 | 4 | 8 | 8 | 2 | 2 | 2 | 2 |
| SA9 | 2 | 2 | ND | ND | 0.5 | 0.5 | ND | ND | 0.5 | ND | ND | ND |
| SA10 | 2 | 2 | ND | ND | 2 | 4 | ND | ND | 1 | ND | ND | ND |
| SA11 | 2 | 2 | ND | ND | 1 | 2 | ND | ND | 1 | ND | ND | ND |
| SA12 | 2 | 2 | ND | ND | 2 | 4 | ND | ND | 1 | ND | ND | ND |
| SA13 | 2 | 2 | ND | ND | 1 | 4 | ND | ND | 1 | ND | ND | ND |
| SA14 | 0.5 | 0.5 | ND | ND | 2 | 2 | ND | ND | 0.25 | ND | ND | ND |
| SA15 | 2 | 2 | ND | ND | 1 | 1 | ND | ND | 1 | ND | ND | ND |
| SA16 | 1 | 2 | ND | ND | 0.25 | 0.5 | ND | ND | 1 | ND | ND | ND |
| SA17 | 2 | 2 | ND | ND | 2 | 4 | ND | ND | 1 | ND | ND | ND |
| SA18 | 2 | 2 | ND | ND | 1 | 4 | ND | ND | 1 | ND | ND | ND |
| SA19 | 2 | 2 | ND | ND | 1 | 4 | ND | ND | 1 | ND | ND | ND |
| SA20 | 2 | 2 | ND | ND | 1 | 4 | ND | ND | 2 | ND | ND | ND |
| SA21 | 2 | 2 | ND | ND | 2 | 8 | ND | ND | 1 | ND | ND | ND |
| SA22 | 2 | 2 | ND | ND | 2 | 4 | ND | ND | 1 | ND | ND | ND |
| SA23 | 2 | 2 | ND | ND | 2 | 4 | ND | ND | 1 | ND | ND | ND |
| SA24 | 2 | 2 | ND | ND | 1 | 4 | ND | ND | 1 | ND | ND | ND |

MIC: minimal inhibitory concentration

Example 3

Plasmid curing was performed per Trevors (Trevors, 1986 Plasmid curing in bacteria. FEMS Microbiology, 32: 149-157). In brief, the clinical isolate was grown in the presence of HN18 and HN34 at the specified concentration for 18 h at 35° C. and then plated on Muller Hinton agar (MHA) plates to obtain isolated colonies. The isolated colonies were then replica plated onto MHA and MHA plates containing antibiotics. The colonies that failed to grow in the presence of antibiotics were considered as putative cured derivatives. The physical loss of plasmid in the cured derivative was confirmed by agarose gel electrophoresis of the plasmid DNA preparation of respective cultures. The percentage curing efficiency was expressed as the number of colonies with cured phenotype per 100 colonies tested. For plasmid extraction, 5 ml of an overnight culture of S. aureus strain was centrifuged and cells were subjected to 1 ml lysostaphin (20 μg/ml) for 1 hour at 35° C. prior to DNA extraction. Extraction of DNA was carried using QIAprep Spin Miniprep Kit (Qiagen) per manufacturer's instruction. DNA profile analysis was carried out by electrophoresis on 1.5% agarose gel.

Plasmid curing activity of HN18 and HN34 was evaluated. Methicillin-resistant S. aureus strains were sub-cultured on blood agar plates to obtain isolated colonies, incubated at 35° C. in a $CO_2$ incubator. The fresh overnight bacterial inoculum was prepared by re-suspending a few isolated colonies in a tube containing 5 ml of saline. The inoculum density was adjusted to a 0.5 McFarland turbidity standard ($1 \times 10^8$ colony forming units (CFU/ml). The bacterial suspension was diluted 1:100 in Mueller-Hinton broth by transferring 50 μl to 5 ml of cation-adjusted Mueller-Hinton broth (CAMHB). The final inoculum was of $1 \times 10^6$ CFU/ml and then 50 μl inoculum was inoculated in 96 well microplates containing increasing concentrations of test compound (HN18 or HN34), ranging from 0.125 to 16 μg/ml. Plates were then incubated at 35° C. for 18 hrs. The antibacterial activity was measured in terms of MIC and SIC by observing visible bacterial growth under the magnifying mirror. Minimal inhibitory concentration (MIC) is the minimum concentration of antimicrobial compound that completely inhibited the growth of bacteria. The sub-inhibitory concentration (SIC) is defined as the concentration before MIC (in a serial dilution method where antibiotic concentration decreases by half from each tube to the next one).

The methicillin-resistant S. aureus clinical isolates (MRSA) growing in the presence of sub-inhibitory concentrations of HN18 and HN34 were taken for the evaluation for the loss of plasmids as described above. A culture control without a curing agent was also maintained in the curing experiment to estimate the rate of spontaneous loss of plasmids under these conditions. HN18 and HN34 eliminated the plasmid mediated antibiotic resistance markers with varying curing efficiencies (Table 3). HN18 cured plasmids from SA1, SA2, SA7 and SA8 at frequency in the range of 13-100%. HN34 also cured plasmids from SA1, SA2, SA7 and SA8 strains with 30%-100% curing efficiency.

It was observed that the results were generally reproducible when plasmid curing experiment were repeated three times. The physical loss of plasmid in the cured derivative was confirmed by agarose gel electrophoresis of the plasmid DNA preparation of respective cultures. Frequency of plasmid curing was thus greatly influenced by even a little change in the concentration of plasmid curing agent.

Plasmid curing activity of HN18 and HN34 was also evaluated in S. aureus (K1902) which is known to harbor a 5 kb plasmid with a chloramphenicol resistance gene. Along with the KSA reference strain, the plasmid curing activity was repeated for SA1 and SA2 strains which are MRSA (Table 4).

Figure 3:
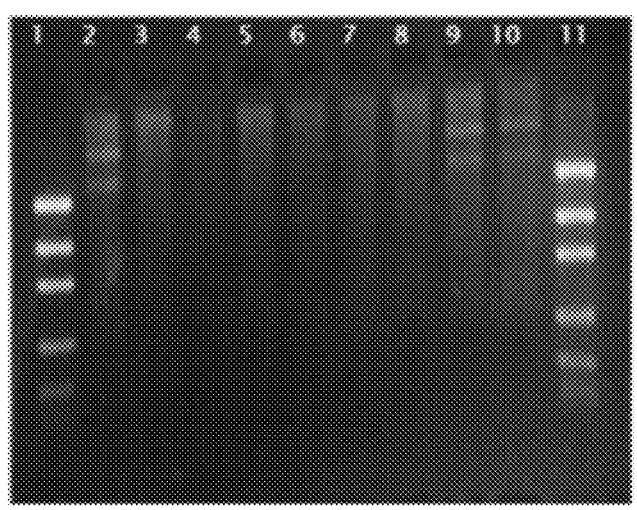
FIG. 3 depicts a DNA profile of *S. aureus* K1902 and plasmid-cured derivatives ("C" designation).

HN18 and HN34 cured plasmid with chloramphenicol resistance gene from S. aureus (K1902) reference strain (33-50% curing efficiency). The physical loss of plasmid in the cured derivative of S. aureus (K1902) was confirmed by agarose gel electrophoresis of the plasmid DNA preparation of respective cultures (FIG. 3). Plasmid DNA was isolated from the original hosts KSA (untreated) as well as from their respective cured derivatives (treated with HN compound) by using QIAprep Spin Miniprep Kit (Qiagen) per the manufacturer's instructions. Plasmid DNA was separated by (1.5%) agarose gel electrophoresis and visualized under UV transillumination. Representative plasmid profiles of the original host as well as their cured derivatives are illustrated in FIG. 3. S. aureus K1902 showed presence of a single plasmid. The corresponding band was absent in HN18 and HN34 treated cured derivatives. Table 3 shows the effects of HN18 and HN34 on the susceptibility of the tested isolates (8 isolates, all MRSA) to methicillin/oxacillin. Isolates showed susceptibility to oxacillin when tested on culture plates containing 4 μg/ml of oxacillin. Prior to exposure to HN18 and HN34, these isolates were resistant to oxacillin and showed MIC values >16 μg/ml.

TABLE 3

| Clinical isolate/plasmid | HN18 SIC µg/ml | HN18 Curing efficiency I | HN18 Curing efficiency II | HN34 SIC µg/ml | HN34 Curing efficiency I | HN34 Curing efficiency II | Lack of growth in presence of drug |
|---|---|---|---|---|---|---|---|
| SA1 | 0.5 | 0 | 100 | 1 | 100 | 100 | M, Ox (4 µg/ml) |
| SA2 | 1.0 | 100 | 50 | 1 | 100 | 70 | M, Ox (4 µg/ml) |
| SA3 | 1.0 | 0 | 0 | 1 | 0 | 0 | M, Ox (4 µg/ml) |
| SA4 | 0.5 | 100 | 0 | 1 | 100 | 0 | M, Ox (4 µg/ml) |
| SA5 | 1.0 | 0 | 0 | 1 | 0 | 0 | M, Ox (4 µg/ml) |
| SA6 | 0.5 | 0 | 0 | 0.5 | 0 | 0 | M, Ox (4 µg/ml) |
| SA7 | 0.5 | 23 | 90 | 0.5 | 50 | 30 | M, Ox (4 µg/ml) |
| SA8 | 1.0 | 13 | 70 | 1 | 40 | 63.33 | M, Ox (4 µg/ml) |

Table 4 shows that methicillin resistant *Staphylococcus aureus* isolates (SA1 and SA2) and Chloramphenicol resistant *Staphylococcus* isolate (KSA) became susceptible to oxacillin and chloramphenicol respectively after exposure to SIC of HN18 and HN34. Isolates SA1, SA2 had oxacillin MIC>16 µg/ml prior to exposure to sub-inhibitory concentration HN18 and HN34. Isolate KSA had a chloramphenicol MIC of >40 µg/ml prior to exposure to SIC of HN18 and HN34. Table 4 also shows the curing efficiency of HN18 and HN34 for these isolates.

TABLE 4

| Clinical Isolate | MIC (µg/ml) I | MIC (µg/ml) II | SIC (µg/ml) I | SIC (µg/ml) II | Curing efficiency (%) I | Curing efficiency (%) II | Lack of growth in presence of drug |
|---|---|---|---|---|---|---|---|
| HN18 | | | | | | | |
| SA1 | 2 | 2 | 1 | 1 | 63.3 | ND | M, Ox (4 µg/ml) |
| SA2 | 2 | 2 | 1 | 1 | 100 | ND | M, Ox (4 µg/ml) |
| KSA | 2 | 2 | 1 | 1 | 36.6 | 46.6 | Cm (10 µg/ml) |
| HN34 | | | | | | | |
| SA1 | 2 | 2 | 1 | 1 | 100 | ND | M, Ox (4 µg/ml) |
| SA2 | 2 | 2 | 1 | 1 | 96.6 | ND | M, Ox (4 µg/ml) |
| KSA | 2 | 2 | 1 | 1 | 33.3 | 50 | Cm (10 µg/ml) |

Experiment conducted in duplicate (I and II);
* M = methicillin,
O = oxacillin;
MIC = minimal inhibitory concentration;
SIC = sub-inhibitory concentration;
KSA-*S. aureus* K1902;
Cm = chloramphenicol;
ND = not detected Example 4

The synergistic effect (interaction) of HN18 and HN34 with different antibiotics against *S. aureus* clinical isolates was studied. The oxacillin MIC values of 8 clinical isolates of *Staphylococcus aureus* were determined. The oxacillin MIC of the same isolates were also determined after they were exposed to SIC of HN18, HN34 (Table 5). In order to demonstrate synergistic activity, one of the two compounds must show at least a four-fold decrease in MIC. Table 5 shows the oxacillin MIC value for the tested strains before and after exposure to SIC of HN18 and HN34. Column 1 shows the oxacillin MIC value for the tested isolates when tested alone. Column 2 and 3 show the oxacillin MIC value of the same isolates in presence of SIC of HN18 and HN34 respectively.

There was a decrease in the oxacillin MIC in synergistic study with HN18. However, HN34 did not show synergistic activity when tested in combination with oxacillin.

TABLE 5

| Isolate | Column 1 Oxacillin MIC (µg/ml) | Column 2 Oxacillin MIC (µg/ml) in presence of SIC of HN18 (1 µg/ml) I | Column 2 Oxacillin MIC (µg/ml) in presence of SIC of HN18 (1 µg/ml) II | Column 3 Oxacillin MIC (µg/ml) in presence of SIC of HN34 (1 µg/ml) I | Column 3 Oxacillin MIC (µg/ml) in presence of SIC of HN34 (1 µg/ml) II |
|---|---|---|---|---|---|
| SA3 | >16 | 0.5 | 0.5 | >16 | >16 |
| SA4 | >16 | 0.5 | 1 | >16 | >16 |
| SA5 | >16 | 0.03 | 0.03 | 16 | >16 |
| SA9 | >16 | 2 | 4 | >16 | >16 |
| SA10 | 16 | <0.03 | <0.03 | 16 | 16 |
| SA11 | 8 | <0.03 | <0.03 | 16 | 8 |
| SA15 | >16 | <0.03 | <0.03 | 16 | >16 |
| SA18 | >16 | <0.03 | <0.03 | >16 | >16 |

The compounds disclosed herein are potent and effective plasmid-curing agents as demonstrated by the loss of resistance plasmids from methicillin/oxacillin resistant strains of *S. aureus*. The sub-inhibitory concentration (SIC) of compounds used in the plasmid curing experiments did not kill the organisms. However, SIC concentration caused the bacteria to lose their plasmid and become susceptible to the antibiotics that they were resistant prior to exposure to the compounds.

Example 5. Computational Studies

Many candidate drugs fail in clinical trials due to poor ADME (Absorption, Distribution, Metabolism, and Excretion) properties. ADME prediction is useful for focusing optimization efforts to enhance the desired properties of a given compound. Incorporating ADME predictions as a part of the development process can generate lead compounds that are more likely to exhibit satisfactory ADME performances during clinical trials. Moreover, the ability to detect problematic candidates early can reduce the amount of time and resources, and streamline the overall development process.

Compounds HN18, HN19, and HN34 were evaluated computationally for pharmaceutically relevant properties. Amoxicillin was used as a reference compound. The compounds were evaluated for ADME properties. Compounds HN18, HN19, HN34, and the reference compound were evaluated with the QikProp program from the Schrodinger drug design software suite (QikProp 4.6 User Manual, Rapid ADME prediction of drug candidates, Schrodinger, Inc. New York, N.Y.). The results for HN18, HN19, and HN34 are shown in Table 6.

TABLE 6

| Comp. | # stars | MW (Da) | Donor HB | Acceptor HB | CNS | QPlog HERG | QPPC aco | QPPMD CK | #met ab | % Human abs. |
|---|---|---|---|---|---|---|---|---|---|---|
| HN18 | 3 | 358.39 | 2 | 0 | 1 | −6.45 | 2874.93 | 4738.16 | 1 | 100 |
| HN19 | 1 | 406.39 | 1 | 6.25 | 1 | −7.45 | 163.38 | 235.98 | 5 | 87.91 |
| HN34 | 4 | 386.44 | 2 | 0 | 1 | −5.94 | 3998.00 | 6668.13 | 3 | 100 |
| Amoxicillin | 1 | 365.40 | 4.25 | 8 | −2 | −0.04 | 0.472 | 0.778 | 5 | 5.61 | stars (0-5 recommended) based on properties and descriptors for FDA approved drugs
CNS (−2 to +2); predicted CNS activity
Donor HB (0 to 6)
Acept HB (2 to 20)
QPlogHERG (concern below −5); predicted IC50 value for blockage of HERG K$^+$ channels
QPPCaco (<25 to >500); Caco-2 cell permeability
QPPMDCK (<25 to >500); MDCK cell permeability
metab (1 to 8); number of likely metabolic reactions
% Human Oral Absorption (0 to 100%)

The results indicate favorable drug-like properties such as CNS penetration, cell permeability, the number of metabolites, and exceptionally high percent human oral absorption. A drug parameter of concern is predicted IC50 value for blockage of HERG K+ channels (qPlogHERG). Compounds with qPlogHERG values below −5 may cause an abnormal repolarizing current in the cardiac action potential. When the HERG channel's ability to conduct electrical current across the cell membrane is inhibited by drugs, it can result in a potentially fatal disorder called long QT syndrome (Sanguinetti & Tristani-Firouzi, *Nature* 440 (7083):463-9, 2006; Sanguinetti et al., *Cell* 81 (2):299-307, 1995; Trudeau et al., *Science* 269(5220):92-5, 1995; Robertson et al., *Novartis Found. Symp.* 266:4-15, 2005; discussion 15-8, 44-5; Morais et al., *Cell* 95 (5):649-55, 1998; Moss et al., *Circulation* 105 (7):794-9, 2002; Sanguinetti & Tristani-Firouzi, *Nature* 440 (7083):463-9, 2006).

In summary, based on the ADME predictions, HN18, HN19, and HN34 have highly favorable drug-like properties. Potential inhibition of the HERG potassium channel that contributes to regulating heart beat is the only predicted concern for the compounds. Computational modeling studies and laboratory experiments can further enhance the pharmacological properties of these compounds.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically significant reduction in a disclosed compound's or composition's ability to reduce, control, or eliminate the presence or activity of unwanted bacteria and/or reduce control or eliminate unwanted side effects of unwanted bacteria.

Unless otherwise indicated, all numbers used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; 19% of the stated value; 18% of the stated value; 17% of the stated value; 16% of the stated value; 15% of the stated value; 14% of the stated value; 13% of the stated value; ±12% of the stated value; 11% of the stated value; ±10% of the stated value; 9% of the stated value; 8% of the stated value; 7% of the stated value; 6% of the stated value; 5% of the stated value; 4% of the stated value; ±3% of the stated value; 2% of the stated value; or 1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to publications, patents and/or patent applications (collectively "references") throughout this specification. Each of the cited references is individually incorporated herein by reference for their particular cited teachings.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A combination pharmaceutical composition, comprising:
   oxacillin;
   HN18 (3-((3,4-difluorophenyl)(2,7a-dihydro-1H-indol-3-yl)methyl)-3a,7a-dihydro-1H-indole), or a pharmaceutically acceptable salt or a pharmaceutically acceptable prodrug thereof; and
   at least one pharmaceutically acceptable excipient.

2. A method of treating a bacterial infection in a subject in need thereof, comprising administering to the subject a therapeutically effective amount of the combination pharmaceutical composition of claim 1.

3. The method of claim 2, further comprising administering:
   an additional antibacterial agent selected from one or more of an aminoglycoside, an ansamycin, a carbacephem, a carbapenem, a cephalosporin, a glycopeptide, a lincosamide, a lipopeptide, a macrolide, a monobactam, a nitrofuran, an oxazolidonone, a penicillin, a penicillin combination, a quinolone, a sulfonamide, a tetracycline, and a combination thereof; and/or
   an antibacterial agent selected from one or more of clofazimine, dapsone, capreomycin, cycloserine, ethambutol, ethionamide, isoniazid, pyrazinamide, rifampicin (rifampin), rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, and trimethoprim.

4. The method of claim 2, wherein the bacterial infection is caused by:
   a gram-negative and/or a gram-positive bacterium;
   a bacterial species selected from one or more of *Acinetobacter, Bordetella, Brucella, Citrobacter, Edwardsiella, Enterobacter, Escherichia, Helicobacter, Klebsiella, Moraxella, Legionella, Neisseria, Pasteurella, Proteus, Providencia, Pseudomonas, Salmonella, Serratia, Shigella, Stenotrophomonas, Vibrio*, and *Yersinia*;
   a multiple drug resistant (MDR) Gram-negative bacterium;
   one or more of *P. aeruginosa*, Extended Spectrum Beta Lactamase (ESBL) *K. pneumonia*, ESBL *E. coli*, and *A. baumannii*;
   a Gram-positive bacterial species selected from one or more of *Streptococcus, Staphylococcus, Corynebacterium, Listeria, Bacillus, Enterococcus*, and *Clostridium*;
   an MDR Gram-positive bacterium;
   methicillin-resistant *S. aureus* (MRSA); or
   vancomycin-resistant Enterococci.

5. A method of plasmid curing a bacterium comprising contacting the bacterium with a therapeutically effective amount of the combination pharmaceutical composition of claim 1, thereby plasmid curing the bacterium.

6. The method of claim 5 wherein:
the plasmid curing occurs in vitro;
the plasmid curing occurs in vivo;
the plasmid curing occurs in vivo in a subject;
the plasmid curing occurs in vivo in a subject suffering from a bacterial infection;
the bacterium is a Gram-negative bacterium or a Gram-positive bacterium; and/or
the plasmid is an antibiotic resistance plasmid.

7. A method of decreasing minimal inhibitory concentration (MIC) of oxacillin, comprising:
administering oxacillin in combination with an effective amount of HN18 (3-((3,4-difluorophenyl)(2,7a-dihydro-1H-indol-3-yl)methyl)-3a,7a-dihydro-1H-indole), or a pharmaceutically acceptable salt or a pharmaceutically acceptable prodrug thereof.

8. The method of claim 7, wherein the MIC of oxacillin is decreased by at least four-fold.

9. The method of claim 7, wherein the MIC of oxacillin is decreased by at least ten-fold.

\* \* \* \* \*